US007166761B2

United States Patent
Noda et al.

(10) Patent No.: US 7,166,761 B2
(45) Date of Patent: Jan. 23, 2007

(54) METHOD OF SCREENING PTPζ ACTIVITY PROMOTER OR INHIBITOR

(75) Inventors: Masaharu Noda, Okazaki (JP); Akihiro Fujikawa, Okazaki (JP)

(73) Assignee: Japan Science and Technology Agency, Kawaguchi (JP)

(*) Notice: Subject to any disclaimer, the term of this patent is extended or adjusted under 35 U.S.C. 154(b) by 548 days.

(21) Appl. No.: 10/333,786

(22) PCT Filed: Jul. 23, 2001

(86) PCT No.: PCT/JP01/06343

§ 371 (c)(1), (2), (4) Date: Jan. 24, 2003

(87) PCT Pub. No.: WO02/08415

PCT Pub. Date: Jan. 31, 2002

(65) Prior Publication Data

US 2003/0186284 A1 Oct. 2, 2003

(30) Foreign Application Priority Data

Jul. 24, 2000 (JP) .............................. 2000-223184

(51) Int. Cl.
  G01N 33/00 (2006.01)
  A01K 67/027 (2006.01)
  A01K 67/033 (2006.01)
  A01K 67/00 (2006.01)
(52) U.S. Cl. ................................. 800/3; 800/18; 800/9
(58) Field of Classification Search ................ None
See application file for complete search history.

(56) References Cited

FOREIGN PATENT DOCUMENTS

WO    WO 02/46390 A2    6/2002

OTHER PUBLICATIONS

Moreadith, 1997, Gene targeting in embryonic stem cells : the new physiology and metabolism, Journal of Molecular Medicine, vol. 75, pp. 208-216.*
Prelle, K. 1999, Establishment of pluripotent cell lines from vertebrate species-present status and future prosopects, Cells Tissues Organs, vol. 165, pp. 220-236.*
Wheeler, M.B. 2001, Transgenic technology and applications in swine. Theriogenology, vol. 56, pp. 1345-1369.*
Nobuaki Maeda et al., "Involvement of Receptor-Like Protein Tyrosine Phosphatase ζRPTPγ And Its Ligand Pleiotrophin/Heparin-Binding Growth-Associated Molecule (HB-GAM) In Neuronal Migration", The Journal of Cell Biology, The Rockefeller University Press, vol. 142, No. 1, pp. 203-216, (1998).
W.-J. Song et al., "Somatodendritic Depolarization-Activated Potassium Currents In Rat Neostriatal Cholinergic Interneurons Are Predominantly Of The A Type And Attributable To Coexpression Of Kv4.2 And Kv4.1 Subunits", The Journal of Neuroscience, Society for Neuroscience, vol. 18, No. 9, pp. 3124-3137, (1998).

Birgit Liss et al., "Alternative Sulfonylurea Receptor Expression Defines Metabolic Sensitivity Of K-ATP Channels In Dopaminergic Midbrain Neurons," The EMBO Journal, European Molecular Biology Organization, vol. 18, No. 4, pp. 833-846, (1999).
Taeko Nishiwaki et al., "Characterization And Developmental Regulation Of Proteoglycan-Type Protein Tyrosine Phosphatase ζRPTPγ Isoforms", J. Biochem., The Japanese Biochemical Society, vol. 123, pp. 458-467, (1998).
Kung Meng et al., "Pleiotrophin Signals Increased Tyrosine Phosphorylation of γ-Catenin Through Inactivation Of The Intrinsic Catalytic Activity Of The Receptor-Type Protein Tyrosine Phosphatase γζ", PNAS, vol. 97, No. 6, pp. 2603-2608, (2000).
Hiroyuki Kawachi et al., "Identification Of GIT1 Cat-1 As A Substrate Molecule Of Protein Tyrosine Phosphatase ζ γ, By The Yeast Substrate-Trapping System", PNAS, vol. 98, No. 12, pp. 6593-6598, (2001).
Takafumi Shintani et al., "Neurons As Well As Astrocytes Express Proteoglycan-Type Protein Tyrosine Phosphatase ζRPTPγ: Analysis Of Mice In Which The PTPζRPTPγ Gene Was Replaced With The LacZ Gene", Neuroscience Letters, vol. 247, pp. 135-138, (1998).
Kinnosuke Yashiro et al., "Activation Of Helicobacter Pylori VacA Toxin By Alkaline Or Acid Conditions Increases Its Binding To A 250-KDa Receptor Protein-Tyrosine Phosphatase γ", J. Biol. Chem., vol. 274, No. 51, pp. 36693-36699, (1999).
Nobuaki Maeda et al., "6B4 Proteoglycan Phosphaean, An Extracellular Variant Of Receptor-Like Protein-Tyrosine Phosphatase ζRPTPγ, binds Pleiotrophin/Heparin-Binding Growth-Associated Molecule (HB-GAM)", J. Biol. Chem., vol. 271, No. 35, pp. 21446-21452, (1996).
Nobuaki Maeda et al., "A Receptor-Like Protein-Tyrosine Phosphatase PTPζ RPTPγ Binds A Heparin-Binding Growth Factor Midkine, Involvement Of Arginine 78 Of Midkine In The High Affinity Binding To PTPζ", J. Biol. Chem., vol. 274, No. 18, pp. 12474-12479, (1999).
Philip Ian Padilla et al. "Morphologic Differentiation of HL-60 Cells is Associated with Appearance of RPTPbeta and Induction of Helicobacter Pylori VacA Sensitivity," Journal of Biological Chemistry, May 19, 2000, vol. 275, No. 20, pp. 15200-15206.
Fujikawa et al. "Dopaminergic Dysfunction in the Mice Lacking the Receptor Tyrosine Phosphatase Zeta/RPTPbeta Gene," vol. 27, No. 1, p. 1429 * Abstract*, Nov. 2001, Society for Neuroscience Abstracts.

* cited by examiner

Primary Examiner—Anne-Marie Falk
Assistant Examiner—Valarie Bertoglio
(74) Attorney, Agent, or Firm—Ann S. Hobbs; Robert Kinberg; Venable LLP

(57) ABSTRACT

An object of the present invention is to provide a remedy for dysfunction of central monoamine pathway, a method for screening a PTPζ inhibitor or activator, and a non-human model animal being hyposensitive to a stimulant drug. After administering a subject material to PTPζ knockout mice and wild-type mice, PTPζ activity in the PTPζ knockout mice and the wild-type mice is compared and evaluated to screen a PTPζ inhibitor or activator. Examples of the comparison and the evaluation of the PTPζ activity include the comparison and the evaluation of the function of central monoamine pathway such as changes in the level of central monoamine metabolism, sensitivity to a stimulant drug, the presence of dysfunction of mesolimbic dopamine pathway, level of acclimation to new circumstances, or stress-responsiveness.

3 Claims, 13 Drawing Sheets

A

PTPζ$^{+/+}$

B

PTPζ$^{-/-}$

PTPζ-A▶
PTPζ-S▶

PTPζ-B▶

A

B ent application No. 2000-223184, filed Jul. 24, 2000.

METHOD OF SCREENING PTPζ ACTIVITY PROMOTER OR INHIBITOR

This application is a national stage application under 35 USC 371 of International Application Serial No. PCT/JP01/06343, filed Jul. 23, 2001, which claims priority to JP application No. 2000-223184, filed Jul. 24, 2000.

TECHNICAL FIELD

The present invention relates to a remedy for dysfunction of central monoamine pathway with the use of a non-human animal such as a mouse or the like which is generated by a homologous recombination technique for genes and is deficient in its receptor-type protein tyrosine phosphatase (PTPζ/RPTPβ) gene, a screening of a remedy for gastric ulcer caused by *Helicobacter pylori* or the like, a non-human model animal being hyposensitive to a central stimulant drug (an addictive drug) and a non-human model animal being hyposensitive to VacA, a toxin of *Helicobacter pylori*, or the like.

BACKGROUND ART

When a cell receives a stimulus from outside, its intracellular signaling pathway is activated to induce proliferation, differentiation, apoptosis and the like of the cell. Tyrosine phosphorylation of intracellular proteins acts an extremely important role in various phases of the signaling pathway, and the state of tyrosine phosphorylation of each protein is always regulated by dynamic equilibrium of delicate balance of two families of enzymes, tyrosine kinase (PTK) and tyrosine phosphatase (PTP). It is known that this tyrosine phosphorylation of proteins is involved in controlling the efficiency of neural circuit formation and neurotransmission in brains (SEITAI NO KAGAKU Vol. 48, No. 6, 534–538, (1997); PROTEIN, NUCLEIC ACID AND ENZYME Vol. 43, No. 8, 1136–1143 (1998)), and is important for the formation and the maintenance of the functions in an immune system and other organs (PROTEIN, NUCLEIC ACID AND ENZYME Vol. 43, No. 8, 1131–1135 (1998)). On the other hand, it is reported that the abnormal tyrosine phosphorylation of proteins is involved in defects in neural circuit formation, disturbance of memory and learning, abnormal apoptosis, tumorigenesis or the like (PROTEIN, NUCLEIC ACID AND ENZYME Vol. 43, No. 8, 1186–1192 (1998)).

To date, more than 80 kinds of PTP have been identified, and it is presumed that the number of genes of PTP in human would reach to 500. Similar to PTK, PTP is classified into two types: a receptor type and a non-receptor type. A receptor-type PTP has two or one enzymic domain intracellularly, and is classified into several groups according to the characteristics of its extracellular domain. PTPζ, which has a carbonic anhydrase domain in N-terminal, has been identified as a receptor-type tyrosine phosphatase specific to the central nervous system. The inventors of the present invention have reported that PTPζ is a receptor of growth factors including pleiotrophin and midkine (J. Biol. Chem. 271, 21446–21452, 1996; J. Cell Biol. 142, 203–216, 1998; J. Biol. Chem. 274, 12471–12479, 1999). In addition, PTPζ is known to interact with cell adhesion molecules which belong to the immunoglobulin super family, such as N-CAM, and is thought to be responsible for important functions in differentiation, migration and neurotransmission of neurons. The present inventors have already generated a PTPζ gene-deficient mouse and reported that PTPζ has expressed in both neurons and astrocytes (Neuroscience Letters 274, 135–138, 1998). The PTPζ gene-deficient mouse has grown and propagated normally, and no major morphologic abnormality has been identified. However, the physiological role of PTPζ has been hardly elucidated so far.

Recently, Hirayama has shown a possibility that PTPζ functions as a receptor of VacA, an exotoxin secreted by *Helicobacter pylori* which is well known as a cause of gastric ulcer, through a test system using cell lines (J. Biol. Chem. 274, 36693–36699, 1999). VacA, a toxin of *Helicobacter pylori*, is detected in about 90% of patients who suffer from acute gastritis or gastric ulcer, and it is reported that a mouse orally administered with VacA, a toxin extracellulary secreted by *Helicobacter pylori*, shows the onset of acute gastritis.

The clarification of in vivo role of PTPζ, whose physiological function has been conventionally unknown, makes it possible to provide findings and experimental materials that lead to the elucidation of onset mechanisms of diseases related to the physiological function of PTPζ, and to the development of remedies of the diseases. An object of the present invention is to provide a remedy for dysfunction of central monoamine pathway, a method for screening a PTPζ inhibitor or activator, which is useful as a remedy for gastric ulcer caused by *Helicobacter pylori* or the like, as a non-human model animal being hyposensitive to a central stimulant drug (an addictive drug) and as a non-human model animal being hyposensitive to VacA, a toxin of *Helicobacter pylori*, or the like, by utilizing the physiological function of PTPζ identified with the use of a PTPζ gene-deficient mouse.

As aforementioned, the present inventors have already generated the mouse with the use of a homologous recombination technique, but it was difficult to eliminate the influence of other genes from the mouse because the mouse was a hybrid wherein chromosomes of two lines of mouse, that is, 129/Sv and C57BL/6J, were mixed. Therefore, a pure line mouse was sufficiently backcrossed (4 generations) to be suitable for analyzing the physiological function of PTPζ, and a PTPζ gene-deficient mouse from which the influence of other genes was eliminated was generated. By comparative analysis of a mouse whose function of gene DNA that encodes the PTPζ was deficient on its chromosome and a wild type mouse, it is revealed for the first time that the PTPζ gene-deficient mouse, which has grown and propagated normally, and where no major morphologic abnormality has been identified, has dysfunction of central monoamine pathway, such as changes in the level of central monoamine metabolism, hyposensitivity to a stimulant drug (methamphetamine), dysfunction of mesolimbic dopamine pathway, delay in acclimating to new circumstances and increase in stress-responsiveness. Further, it was found that PTPζ, which is thought to be a receptor of VacA, a toxin of *Helicobacter pylori*, is expressed in gastric epithelial cell layer of a mouse. The present invention has thus been completed.

DISCLOSURE OF THE INVENTION

The present invention relates to a method for screening a PTPζ inhibitor or activator wherein a subject material is administered to a non-human animal whose function of gene DNA that encodes proteoglycan-type receptor-type protein tyrosine phosphatase (PTPζ) is deficient on its chromosome and a wild-type non-human animal, and PTPζ activities in these non-human animals are compared and evaluated (claim 1), the method for screening a PTPζ inhibitor or activator according to claim 1, wherein the comparison and the evaluation of PTPζ activity is the comparison and the evaluation of the function of central monoamine pathway (claim 2), the method for screening a PTPζ inhibitor or activator according to claim 2, wherein the comparison and the evaluation of the function of central monoamine pathway is the comparison and the evaluation of changes in the level of central monoamine metabolism, sensitivity to a stimulant drug, the presence of dysfunction of mesolimbic dopamine pathway, level of acclimation to new circumstances, or stress-responsiveness (claim 3), the method for screening a PTPζ inhibitor or activator according to claim 1, wherein the comparison and the evaluation of PTPζ activity is the comparison and the evaluation of the level of binding to VacA, a toxin of *Helicobacter pylori* (claim 4), the method for screening a PTPζ inhibitor or activator according to claim 1, wherein the comparison and the evaluation of PTPζ activity is the comparison and the evaluation of the level of binding to pleiotrophin, a heparin-binding secretory protein (claim 5), the method for screening a PTPζ inhibitor or activator according to any one of claims 1 to 5, wherein the non-human animal whose function of gene DNA that encodes PTPζ is deficient on its chromosome is purified by being backcrossed for 4 or more generations (claim 6), the method for screening a PTPζ inhibitor or activator according to any one of claims 1 to 6, wherein the non-human animal is a mouse (claim 7), a PTPζ inhibitor or activator obtained by the method for screening a proteoglycan-type receptor-type protein tyrosine phosphatase (PTPζ) inhibitor or activator according to any one of claims 1 to 7 (claim 8), the PTPζ inhibitor or activator according to claim 8, wherein the PTPζ inhibitor or activator is a binding inhibitor between PTPζ and VacA, a toxin of *Helicobacter pylori* (claim 9), the PTPζ inhibitor or activator according to claim 8, wherein the PTPζ inhibitor or activator is a binding inhibitor between PTPζ and pleiotrophin, a heparin-binding secretory protein (claim 10), a remedy for dysfunction of central monoamine pathway containing the proteoglycan-type receptor-type protein tyrosine phosphatase (PTPζ) inhibitor or activator according to claim 8 as an active component (claim 11), a remedy for gastric ulcer or gastritis caused by *Helicobacter pylori* containing the proteoglycan-type receptor-type protein tyrosine phosphatase (PTPζ) inhibitor according to claim 8 or 9 as an active component (claim 12), a remedy for gastric ulcer or gastritis caused by pleiotrophin containing the proteoglycan-type receptor-type protein tyrosine phosphatase (PTPζ) inhibitor according to claim 8 or 10 as an active component (claim 13).

The present invention also relates to a non-human model animal whose function of gene DNA that encodes proteoglycan-type receptor-type protein tyrosine phosphatase (PTPζ) is deficient on its chromosome and which is hyposensitive to a central stimulant drug (an addictive drug) (claim 14), the non-human model animal according to claim 14, wherein the non-human animal is hyposensitive to a stimulant drug (claim 15), the non-human model animal according to claim 14 or 15, wherein the non-human animal whose function of gene DNA that encodes PTPζ is deficient on its chromosome is purified by being backcrossed for 4 or more generations (claim 16), the non-human model animal according to any one of claims 14 to 16, wherein the non-human animal is a mouse (claim 17), a non-human model animal whose function of gene DNA that encodes proteoglycan-type receptor-type protein tyrosine phosphatase (PTPζ) is deficient on its chromosome and which is hyposensitive to VacA, a toxin of *Helicobacter pylori* (claim 18), a non-human model animal whose function of gene DNA that encodes proteoglycan-type receptor-type protein tyrosine phosphatase (PTPζ) is deficient on its chromosome and which is hyposensitive to pleiotrophin, a heparin-binding secretory protein (claim 19), the non-human model animal according to claim 18 or 19, wherein the non-human animal whose function of gene DNA that encodes PTPζ is deficient on its chromosome is purified by being backcrossed for 4 or more generations (claim 20), and the non-human model animal according to any one of claims 18 to 20, wherein the non-human animal is a mouse (claim 21).

BEST MODE FOR CARRYING OUT THE INVENTION

Figure 1:
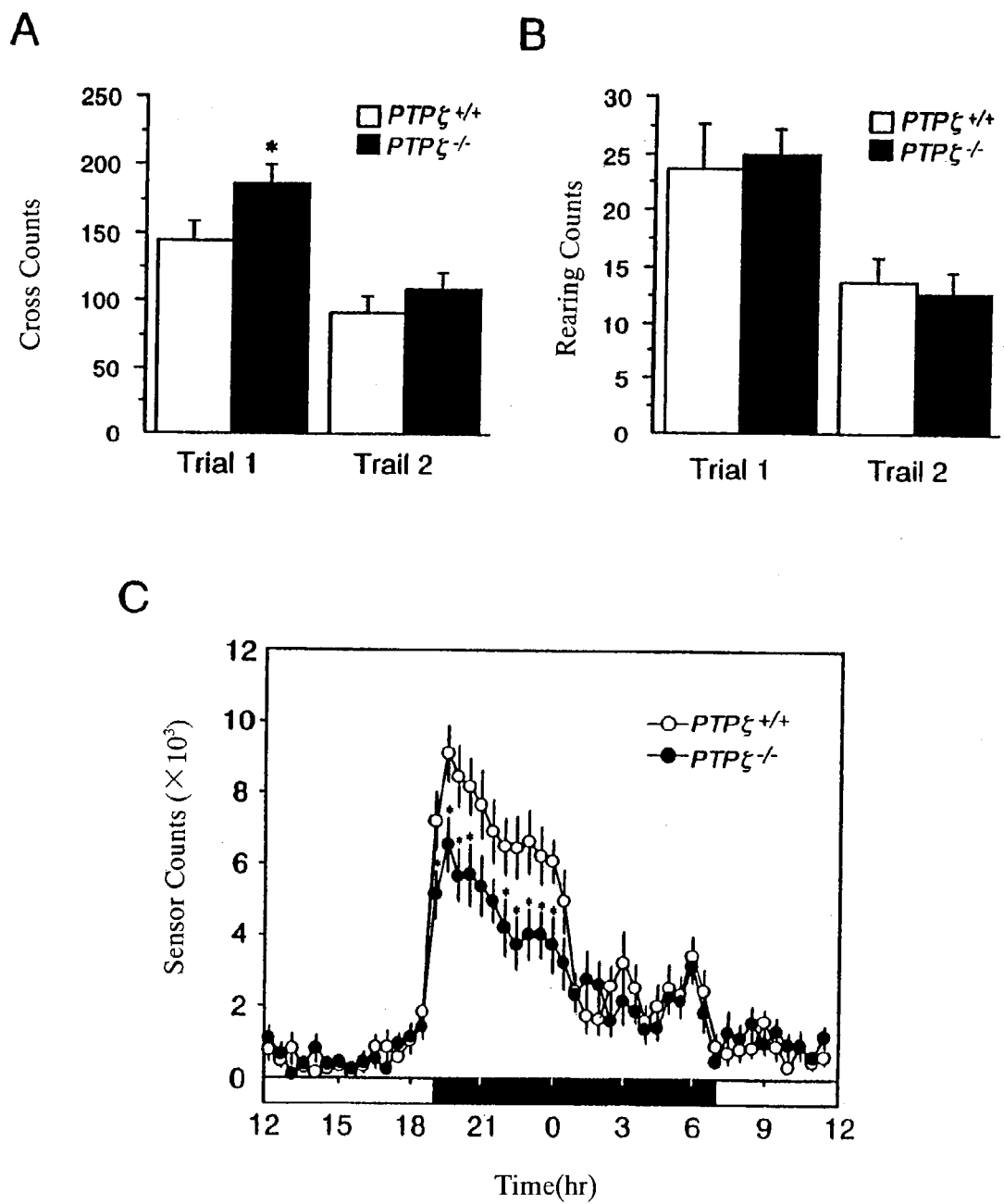
FIG. 1 is a view showing the examination results of character phenotypes of PTPζ-deficient mice in an open field test and circadian rhythm.

The method for screening a PTPζ inhibitor or activator according to the present invention is not particularly limited as long as it is a method for screening wherein a subject material is administered to a non-human animal whose function of gene DNA that encodes PTPζ is deficient on its chromosome and a wild-type non-human animal, and PTPζ activities in these non-human animals are compared and evaluated (analyzed). An example of the non-human animal whose function of gene DNA that encodes PTPζ is deficient on its chromosome includes a non-human animal wherein a part or the whole of its endogenous gene that encodes PTPζ is inactivated by gene mutation such as disruption, deficiency, substitution or the like, and the function of expressing PTPζ in wild type is lost. In addition, as the non-human animal according to the present invention, rodents including a mouse, a rat and a guinea pig are specifically exemplified, but not limited to these animals. The method for constructing a non-human animal whose function of gene that encodes PTPζ is deficient on its chromosome is explained below with an example of a mouse whose function of PTPζ gene is deficient on its chromosome.

A mouse whose function of PTPζ gene is deficient on its chromosome, in other words, a PTPζ knockout mouse can be constructed by the method described in the aforementioned paper written by the present inventors (Neuroscience Letters 274, 135–138, 1998), or other such methods. Specifically, the construction method comprises the steps of: a PTPζ gene is screened by using a gene fragment obtained from mouse gene library through PCR or the like; a part or the whole of the screened PTPζ gene is substituted with a marker gene, for example, a Lac-Z gene, a neomycin-resistant gene or the like, and if necessary, a gene such as a diphthelia toxin A fragment (DT-A) gene or a herpes simplex virus thymidine kinase (HSV-tk) gene is introduced into 5'-terminal side, to construct a targeting vector; this constructed targeting vector is linearized and introduced into an ES cell by microinjection, electroporation or other such methods and then homologously recombined; among the homologous recombinants, an ES cell resistant to X-gal staining or antibiotics such as G418, ganciclovir (GANC) or the like is selected. It is preferable to confirm whether the selected ES cell is the intended recombinant by Southern blotting or other such methods.

The above-mentioned recombined ES cell is microinjected into a mouse blastocyst, and then the blastocyst is transplanted into a recipient to generate a chimeric mouse. A heterozygous mouse can be obtained by intercrossing the chimeric mouse and a wild-type mouse, and a PTPζ knockout mouse can be obtained by intercrossing the heterozygous mice. Further, by backcrossing the obtained knockout mouse with a pure line mouse, PTPζ knockout mice whose genetic background other than PTPζ is in uniform can be obtained. Any pure line mouse can be used as the pure line mouse, for instance, C57BL/6J is specifically exemplified. Examples of the method for confirming whether PTPζ is present in the PTPζ knockout mouse include; Southern blotting or the like of DNA separated from a part of a tail tip of a mouse obtained by the above-mentioned methods, Northern blotting or the like of RNA isolated from neurons or the like of the mouse, and Western blotting or the like of PTPζ expression in the mouse.

As the method for screening a PTPζ inhibitor or activator according to the present invention, a method wherein a subject material is respectively administered to a non-human animal whose function of gene that encodes PTPζ is deficient on its chromosome, for example, a PTPζ knockout mouse, and a wild-type mouse, preferably a wild-type littermate, and PTPζ activities in the PTPζ knockout mouse and in the wild-type mouse are compared and evaluated is exemplified. Examples of the comparison and the evaluation of the PTPζ activities mentioned above are, the comparison and the evaluation of the function of central monoamine pathway including the comparison and the evaluation of changes in the level of central monoamine metabolism, sensitivity to a stimulant drug, the presence of dysfunction of mesolimbic dopamine pathway, level of acclimation to new circumstances or stress-responsiveness; the comparison and the evaluation of the level of binding to VacA, a toxin of *Helicobacter pylori*, particularly the level of binding inhibition between PTPζ and VacA, a toxin of *Helicobacter pylori*, and the comparison and the evaluation of the level of binding to pleiotrophin, a heparin-binding secretory protein, particularly the level of binding inhibition between PTPζ and pleiotrophin, a heparin-binding secretory protein, that are explained in detail in the examples.

The method for administering a subject material in the method for screening a PTPζ inhibitor or activator is not particularly limited, and oral or intravenous administration or the like can be used. In such method, after administering a subject material, PTPζ activities in the PTPζ knockout mouse and in the wild-type mouse are measured, and then compared and evaluated. The higher cerebral function in which monoamine pathway is involved varies widely, and it is known that its dysfunction and degeneration lead to various disease states. Consequently, in the case where dysfunction of central monoamine pathway in a PTPζ knockout mouse is ameliorated/cured to the same level as the function of a wild-type mouse, the subject material is thought to be a PTPζ activator such as a PTPζ agonist, and the PTPζ activator shows promise as a remedy for dysfunction of central monoamine pathway, for example, as a novel remedy not only for Parkinson's disease or Huntington's disease, which are serious neurodegenerative diseases, autism or the like, but also for nervous affections including manic-depression, attention-deficit disorder, and drug addiction. In addition, there is a possibility that the PTPζ inhibitor discovered by the comparison and the evaluation of the function of central monoamine pathway is useful as a remedy for gastric ulcer and gastritis caused by VacA, a toxin of *Helicobacter pylori*, or pleiotrophin, a heparin-binding secretory protein mentioned below.

VacA, an exotoxin secreted by *Helicobacter pylori* which is well known as a cause of gastric ulcer, is detected in about 90% or more of the patients who suffer from acute gastritis or gastric ulcer, and it is known that a mouse orally administered with VacA, a toxin extracellularly secreted by *Helicobacter pylori*, shows the onset of acute gastritis. Consequently, in the case where the level of binding to VacA, a toxin of *Helicobacter pylori*, in a wild-type mouse is ameliorated to a same level as that in a PTPζ knockout mouse, it means that the subject material is a PTPζ inhibitor such as a PTPζ antagonist and a binding inhibitor between PTPζ and VacA, a toxin of *Helicobacter pylori*, and the PTPζ inhibiting substance/PTPζ inhibitor shows promise as a novel remedy for gastric ulcer and gastritis. There is a possibility that the above-mentioned PTPζ activator discovered by the comparison and the evaluation of the level of binding to VacA, a toxin of *Helicobacter pylori*, is useful as a remedy for dysfunction of central monoamine pathway. The present inventors have revealed for the first time that pleiotrophin causes gastric ulcer by binding to PTPζ, and the involvement of pleiotrophin in the formation of gastric ulcer has never been known. A PTPζ-deficient mouse is a negative control of the formation of gastric ulcer caused by pleiotrophin.

Further, the present inventors have revealed for the first time that 18 kD pleiotrophin, a heparin-binding secretory protein, causes gastric ulcer by binding to PTPζ. Therefore, in the case where the level of binding to pleiotrophin in a wild-type mouse is ameliorated to a same level as that in a PTPζ knockout mouse it means that the subject material is a PTPζ inhibitor such as a PTPζ antagonist and a binding inhibitor between PTPζ and pleiotrophin, and the PTPζ inhibiting substance/PTPζ inhibitor shows promise as a novel remedy for gastric ulcer and gastritis. There is a possibility that the above-mentioned PTPζ activator discovered by the comparison and the evaluation of the level of binding to plelotrophin is useful as a remedy for dysfunction of central monoamine pathway.

The non-human model animal hyposensitive to a stimulant drug (an addictive drug) according to the present invention is not particularly limited as long as it is a PTPζ knockout mouse whose function of gene DNA that encodes proteoglycan-type receptor-type protein tyrosine phosphatase (PTPζ) is deficient on its chromosome, or the like, but a knockout backcrossed for 4 or more generations is preferable. The usefulness of a PTPζ knockout mouse, in particular, its hyposensitivity to a stimulant drug (an addictive drug) had not been known until it was revealed for the first time by the present inventors. The term "hyposensitivity" here means lower level of reactivity to a stimulant drug in comparison to the reactivity level of wild-type non-human animals. The non-human model animal hyposensitive to a stimulant drug (an addictive drug) according to the present invention includes those from slightly hyposensitive ones to totally unresponsive ones. In addition, as the stimulant drug (the addictive drug), methamphetamine, amphetamine that has a same effect as methamphetamine, cocaine and cannabis that have a same effect as dopamine transporter inhibitor GBR 12909, LSD that has a same effect as p-chloro-amphetamine, which is a serotonin liberator, selective serotonin reuptake inhibitor (SSRI) used as an antidepressant such as fluoxetine, fluoxamine, paroxetine, serrtraline or the like, are exemplified. The non-human model animal hyposensitive to a central stimulant drug (an addictive drug) according to the present invention is hyposensitive to a stimulant drug (an addictive drug), and in addition, shows abnormal neurological properties including the changes in the level of central monoamine metabolism, dysfunction of mesolimbic dopamine pathway, delay in acclimating to new circumstances or increase in stress-responsiveness, as described in detail in examples mentioned below. Consequently, the non-human model animal is not only useful as an experimental model animal for elucidating a signal transmission mechanism in the central nervous system such as a mechanism of response to a central stimulant drug (an addictive drug), but also available for screenings of novel remedies for drug addiction or nervous affections as mentioned above.

The non-human model animal hyposensitive to VacA which is a toxin of *Helicobacter pylori* or pleiotrophin which is a heparin-binding secretory protein according to the present invention is not particularly limited as long as it is a PTPζ knockout mouse whose function of gene DNA that encodes proteoglycan-type receptor-type protein tyrosine phosphatase (PTPζ) is deficient on its chromosome, or the like, but a knockout mouse backcrossed for 4 or more generations is preferable. The usefulness of a PTPζ knockout mouse, in particular, its hyposensitivity to VacA which is a toxin of *Helicobacter pylori* or pleiotrophin which is a heparin-binding secretory protein had not been known until it was revealed by the present invention. The non-human model animal hyposensitive to VacA which is a toxin of *Helicobacter pylori* or pleiotrophin which is a heparin-binding secretory protein according to the present invention is not only useful as an experimental model animal for elucidating the onset mechanism of gastric ulcer caused by VacA which is a toxin of *Helicobacter pylori* or pleiotrophin which is a heparin-binding secretory protein, but also available as an advantageous negative control for the screening of a novel remedy for gastric ulcer as mentioned above.

The present invention is explained below more specifically with reference to examples, however, the present invention is not limited to these examples.

EXAMPLE 1

(Physiological Role of PTPζ in Central Dopamine Pathway and Monoamine Pathway, and Usefulness of a PTPζ-deficient Mouse).

Though large amount of PTPζ is expressed in the central nervous system, its neurophysiologic role has been unknown. Therefore, the importance of PTPζ molecule in higher cerebral function was examined at individual level by comparing and analyzing a PTPζ gene-deficient mouse and a wild-type mouse behaviorally and neuropharmacologically.

EXAMPLE 1-1

[Method]

(A-1 Animals)

A PTPζ-deficient mouse was generated by the method described in the aforementioned paper written by the present inventors (Neuroscience Letters 247, 135–138, 1998). A LacZ gene was inserted into the position immediately after the translation initiation codon in exon 1 of a PTPζ gene of a mutant mouse and accordingly, a LacZ gene was expressed under the control of expression regulatory unit of the PTPζ gene. In this experiment, a knockout mouse was backcrossed with inbred C57BL/6J line for 4 generations, and male littermates of 2 to 5 months old were used. The animals were housed in an animal care facility at 25.degrees C., with a 12/12 hours light-dark cycle and fed food and water ad libitum. Animals were cared in accordance with the institutional guidelines.

(A-2 Behavioral Experiment)

A behavioral experiment was conducted during the light cycle from 7:00 a.m. to 7:00 p.m.

A-2-1

In an open field test, a mouse was placed in the center of a gray round field (internal diameter: 80 cm, height: 40 cm) divided into 25 equal segments by grids. Locomotor activity was measured as the number of line crossings of the grid during 5 minutes.

A-2-2

Circadian motility was measured with an infrared ray passive sensor system (AB system 24A, Neuroscience, Inc.). For the measurement, a sensor was set on the top of a normal mouse cage (30×20×13 cm) where the animals were housed individually with ad libitum food and water for 7 days. Analysis and evaluation were made with the measured data of the last 3 days.

A-2-3

In a forced swimming test, a mouse was forced to swim for 15 minutes in 2 consecutive days in a cylindrical container (diameter: 8 cm, height: 20 cm) which contained water at 22. degree. C. to a depth of 8 cm. Locomotion was measured every 5 minutes with an infrared monitoring apparatus (SCANET MV-10, Toyo Sangyo Co. Ltd.).

A-2-4

An elevated plus maze consisted of a central area (6×6 cm) and 4 arms placed 50 cm above floor. Two "closed arms" were enclosed within walls (30 cm), and the other two "open arms" had low rims (1 cm). A mouse was placed in the center of the maze and the number of entries and time spent in the open and closed arms were counted for 5 minutes under a dim light condition (about 80 lux).

A-2-5

An exploration behavior to a novel object was evaluated with an open field container and a plastic cube (9 cm on a side). On the day before the experiment, a mouse was placed in an open field for about 10 minutes to be acclimated to the circumstance in advance. On the day of the experiment, the mouse was placed in the field that contained nothing, and observed for 9 minutes. Then, a cube-shaped plastic block was placed quietly in the center of the central area of the field, and the mouse was further observed for 9 minutes. As to the result of the observation, the number of times that the mouse crossed the partition lines in the open field was counted and evaluated as mobility, and the number of times that the mouse crossed the partition lines in the whole area of the field and a certain area in the center of the field were evaluated respectively.

(A-3 Pharmacological Experiments)

The effects of psychostimulant drugs on locomotor activity were measured in a clear acrylic chamber (40×40×40 cm) by measuring animal movements with an electromagnetic activity monitoring system (sensor unit 0603, scanner 1099, Panlab). Before drug administration, the animals were acclimated to the measurement circumstance for at least 90 minutes. The animals were then administered with a stimulant drug, methamphetamine (METH) (1 mg/kg, s.c.), GBR12909 (2 mg/kg, i.p.), apomorphine (1 mg/kg, s.c.), or p-chloro-amphetamine (2 mg/kg, i.p.), and saline as administered to a control, and locomotor activity was monitored for the next 60 minutes.

(A-4-1 Quantification of Dopamine and its Metabolites)

Brain tissues were dissected on ice and extracted by sonication in a solution containing 10 mM $HClO_4$, 0.1 mM sodium pyrosulfite, 20 μM EDTA·2Na and 10 pg/ml (±) isoproterenol as an internal standard, and the extract was centrifuged at 15,000 rpm for 10 minutes. Dopamine and its metabolites in the supernatant were measured by automated HPLC with an electrochemical detector (Coulochem II, MC Medical, Inc.) under the following condition. The separation was performed on MCM C-18 column (4.6×150 mm, MC Medical, Inc.) using 50 mM acetate-citrate buffer (pH 3.0) containing 3.1% acetonitrile, 7.6% methanol, 4.4 mM sodium 1-heptanesulfonate, and 0.1 mM EDTA·2Na, at a flow rate of 1.0 ml/min in a column-chamber maintained at 37.degree. C. The working electrode was set at +450 mV.

(A-4-2 In Vivo Microdialysis)

Mice were anaesthetized with sodium pentobarbital (80 mg/kg i.p.) and placed in a stereotaxic apparatus. A hole was drilled through the skull and an intracerebral guide cannula (CMA 11, CMA/Microdialysis AB) was inserted into the nucleus accumbens (NAC) and fixed with dental cement. The stereotaxic coordinates for implantation of the guide cannula in both wild-type and PTPζ-deficient mice were: anterior, +1.1 mm, ventral, +3.6 mm, lateral, +1.0 mm to the surface of bregma. 24 hours after the surgery, mice were chained to a counterbalance lever arm attached to a locomotor activity chamber (30×30 cm) with an infrared monitoring apparatus (SCANET LC-10, Toyo Sangyo Co., Ltd.). Dialysis probes (membrane length 1 mm; external diameter 0.24 mm; cuprophane CUP 11, CMA/Microdialysis AB) were inserted through the guide cannula and perfusion was performed with artificial cerebrospinal fluid (ACSF), pH 7.4, (in mM; 145.0NaCl, 2.7 KCl, 1.2 $CaCl_2$, 1.0 $MgCl_2$, and 2.0 $NaH_2PO_4$) at a flow rate of 2 μl/min. Perfusates were collected from freely moving animals every 20 minutes in a tube containing 20 μl of 0.4 M $HClO_4$ (CMA 170). Samples were collected and assayed using HPLC-ECD as described above except for the following modifications: the column was MCM C-18 (4.6×150 mm) and the buffer contained 75 mM $NaH_2PO_4$, 1.7 mM 1-octanesulfonic acid sodium salt, 0.1 mM triethylamine, 25 μM EDTA·2Na and 10% acetonitrile, at flow rate of 0.55 ml/min at 30.degree. C. The electrode was set at +320 mV. METH administration (1 mg/kg s.c.) or local infusion of high $K^+$ solution (in mM: 47.7 NaCl, 100.0 KCl, 1.2 $CaCl_2$, 1.0 $MgCl_2$, and 2.0 $NaH_2PO_4$, pH 7.4) through the microdialysis probe was performed after the state became steady.

(A-5 Immunohistochemistry)

Mice were anaesthetized with sodium pentobarbital and perfused and fixed with 4% paraformaldehyde solution. Brains were dissected and incubated overnight in 0.1 M phosphate buffer (PB) containing 30% sucrose at 4.degree. C. The brains were cut into 40 μm sections on a cryostat. The sections were treated with 20 mM PB-saline (PBS) containing 3% $H_2O$ and 0.05% NP-40 for 30 minutes, and then blocked with 10% normal goat serum and 0.05% TritonX-100 in PBS. The sections were then incubated overnight with rabbit anti-tyrosine hydroxylase (1:1000) (AB152, Chemicon International Inc.). The binding of specific antibodies was detected by using an ABC peroxidase kit (Vectors Laboratories, Inc.) according to the manufacture's instructions with 3,3-diaminobenzidine (DAB) and $H_2O_2$ as the substrate. To detect the β-galactosidase which reflect the PTPζ-gene expression, tissue sections from the heterozygous mutant mice were subjected to X-gal staining before immunohistochemical analyses (Neuroscience Letters 274, 135–138, 1998).

(A-6 Dopamine Uptake Assay)

Dopamine (DA) uptake was measured as follows. Striatal synaptosome tissue pools (3 animals/pool) were homogenized in 100 volume (v/w) of 0.32 M sucrose in a teflon-glass homogenizer and centrifuged at 12,000 rpm for 10 minutes. The crude synaptosomal pellet was resuspended in 0.32 M sucrose at a concentration of 30 mg/ml (original wet weight) and divided into 30 μl aliquots. Each aliquot was added with 270 μl of Krebs-Ringer phosphate buffer with increasing concentrations of [$^3$H] DA (final 1–10 nM, 88.5 Ci/nmol, Amersham Pharmacia Biotech UK Ltd.). After incubating the resultant solution for 3 minutes at 30.degree. C., uptake was quickly terminated by filtration through Whatman GF/C glass filters. The filters were rinsed three times with 2.5 ml ice-cold 0.32 M sucrose and measured by using a liquid scintillation counter at an efficiency of 50%. Blank values were measured in the presence of 10 μM GBR12909.

(A-7 Synthesis of cDNA from a Single Cell)

The cDNA preparation from single cells was carried out as described previously (J. Neuroscience 18, 3124–3137, 1998). Mice brains were removed quickly after decapitation, and cut into 400 μm thick coronal midbrain slices with a microslicer while bathed in low $Ca^{2+}$ HEPES-buffered saline (in mM: 140.0 Na isethionate, 2.0 KCl, 4.0 $MgCl_2$, 0.1 $CaCl_2$, 23.0 glucose, and 15.0 HEPES). The slices were maintained for one hour at room temperature in $NaHCO_3$ buffered saline (having 126.0 NaCl, 2.5 KCl, 2.0 $MgCl_2$, 26.0 $NaHCO_3$, 1.25 $NaH_2PO_4$, 1.0 pyruvic acid, 0.2 ascorbic acid, 0.1 $N^G$-nitro-L-arginine, 1.0 kynurenic acid, and 10.0 glucose, adjusted to be pH 7.4 with NaOH, in mM). The ventral tegmental area and substantia nigra were cut out and put in low $Ca^{2+}$, and then treated with 1 mg/ml pronase in HEPES-buffered HBSS at 35.degree. C. for 30 minutes in an oxygenated Cell-stir chamber (Wheaton, Inc.). The tissue was rinsed three times with low $Ca^{2+}$ HEPES-buffered saline and its cells were dissociated by repeated pipetting with Pasteur pipettes. The cell suspension was poured into a 35 mm Lux Petri dish containing HEPES-buffered HBSS, which was mounted on the stage of a microscope. After allowing cells to settle down, the solution was replaced by HEPES buffer. The content of the cells were aspirated into an electrode pipette filled with diethyl pyrocarbonate (DEPC)-treated water. The content was immediately recovered and added to a mixture of 5 μl DEPC-treated water ($H_2O$), 0.5 μl RNAsin (28,000 U/ml, Promega Corporation), 0.5 μl dithiothreitol (DTT, 0.1 M), and 0.1 μl random hexamer primer (50 ng/μl). The resulting mixture was heated at 70.degree. C. for 10 minutes, and then iced quickly for 5 minutes. The cDNA was synthesized by adding 1 μl of Superscript II reverse transcriptase (200 U/μl) (Life Technologies), 4 μl of 5×reaction buffer, and 1 μl of 10 mM dNTP to cell mRNA. After conducting the reaction in a total volume of 20 μl at 42.degree. C. for 50 minutes, a treatment was performed at 70.degree. C. for 15 minutes.

(A-8 Multiplex and Nested PCR)

Multiplex and nested PCR were performed as previously described (EMBO J. 18, 833–846, 1999) with modifications. Single-cell cDNA was treated with RNase (1 μl, 2 U/μl) at 37.degree. C. for 20 minutes. The primer sets of marker genes, tyrosine hydroxylase (TH, GenBank accession No. M69200), glutamic acid decarboxylase 67 (GAD67, accession No. Z49976), and glial acidic fiber protein (GFAP, accession No. K01347), were reported by Liss et al. (EMBO J. 18, 833–846, 1999), and the primer sets to amplify PTPζ (accession No. U09357) were constructed in this experiment. The cDNA of TH, GAD67, GFAP, and PTPζ were amplified simultaneously in a single tube by multiplex PCR using the first primer mixture (for PTPζ from 5' to 3'; sense [Seq. ID. No. 1]: GGT CCA CTG AAG TCC ACA GC; position 5512 to 5531, antisense [Seq. ID. No. 2]: TCT AGT ACA ATG TAT GTG CCC G; position 5948 to 5927). The initial multiplex-PCR was performed in a final volume of 20 μl containing 5 μl of the single-cell cDNA, 20 pmol of each primer, 200 μM dNTPs, 2 μl of 10×PCR buffer, and 1 U of EX-Taq (Takara Shuzo, Co., Ltd.). The PCR was conducted with a Thermal Cycler MP (Takara) under the following conditions: 94.degree. C. for 5 minutes followed by 25 cycles at 95.degree. C. for 30 seconds, 62.degree. C. for 3 seconds, and 72.degree. C. for 2 minutes, with a treatment at 72.degree. C. for 5 minutes. The nested-PCR was carried out in four individual reactions in a final volume of 20 μl containing 0.1 μl of the initial PCR product, 200 μM dNTPs, 2 μl of 10×PCR buffer, 0.5 U of EX-Taq, and 10 pmol of each of primer pairs (for PTPζ sense [Seq. ID. No. 3]: CGG GAG CTT CCT GGT CAA CCA G; position 5655 to 5677, antisense [Seq. ID. No. 4]: AGC ACG GGT AGG GAG TAC TC; position 5873 to 5824). To investigate the presence and the size of the amplified fragments, 5 μl aliquots of the PCR products were separated by electrophoresis on 3% Nusive 3:1 agarose gel (FMC BioProducts, Rockland), and visualized with ethidium bromide staining. The predicted sizes (bp) of the eight PCR-generated fragments were: 189 (PTPζ), 377 (TH), 517 (GFAP), and 702 (GAD67). The primers for PTPζ can only amplify the intracellular phosphatase domain D1, which is present only in the sequences of the PTPζ-A and -B isoforms, but not in the PTPζ-S which is also known as phosphacan (J. Biochem. (Tokyo), 123, 458–467, 1998).

EXAMPLE 1-2

[Results]

(Behavioral Phenotype of PTPζ-deficient Mice)

In order to elucidate the behavioral phenotype of PTPζ-deficient mice, behavioral observation was conducted by an open field test (the above-mentionedmethods A-1 and A-2-1). Locomotor activity (A) and rearing (B) of wild-type mice (PTPζ$^{+/+}$, n=10) and PTPζ-deficient mice (PTPζ$^{-/-}$, n=12) were measured for consecutive 2 days by the open field test, and the results are shown in FIGS. 1A and 1B, respectively. The data are presented as mean±SEM (*$p<0.05$). As a result, PTPζ-deficient mice exhibited larger amount of locomotor activity than wild-type mice, and significantly high motility in the open field on the first day. However, 24 hours later, the change disappeared in the test (FIG. 1A). On the other hand, significant change was not found in values for rearing, an exploration behavior (FIG. 1B). It was revealed that the PTPζ-deficient mice increased their responsibility of locomotor activity to novel circumstances.

Locomotor activity in home-cage condition was examined for consecutive days (the above-mentioned method A-2-2). Mice were housed individually for 7 days, and locomotor activity was analyzed with an infrared ray passive sensor system during the last 3 days (PTPζ$^{+/+}$, n=14 and PTPζ$^{-/-}$, n=14). The results are shown in FIG. 1C. The data are presented as mean+SEM per each 30 minutes interval (*$p<0.05$). The PTPζ$^{-/-}$ mice showed a marked decrease in the peak of circadian activity during the early dark phase compared with the wild-type mice, and their activity peak immediately after lights were put off (19:00 to 24:00) was significantly low in comparison with the wild-type mice, though their activity rhythm was normal.

(Abnormal Metabolism of Monoamine in Brain)

Figure 2:
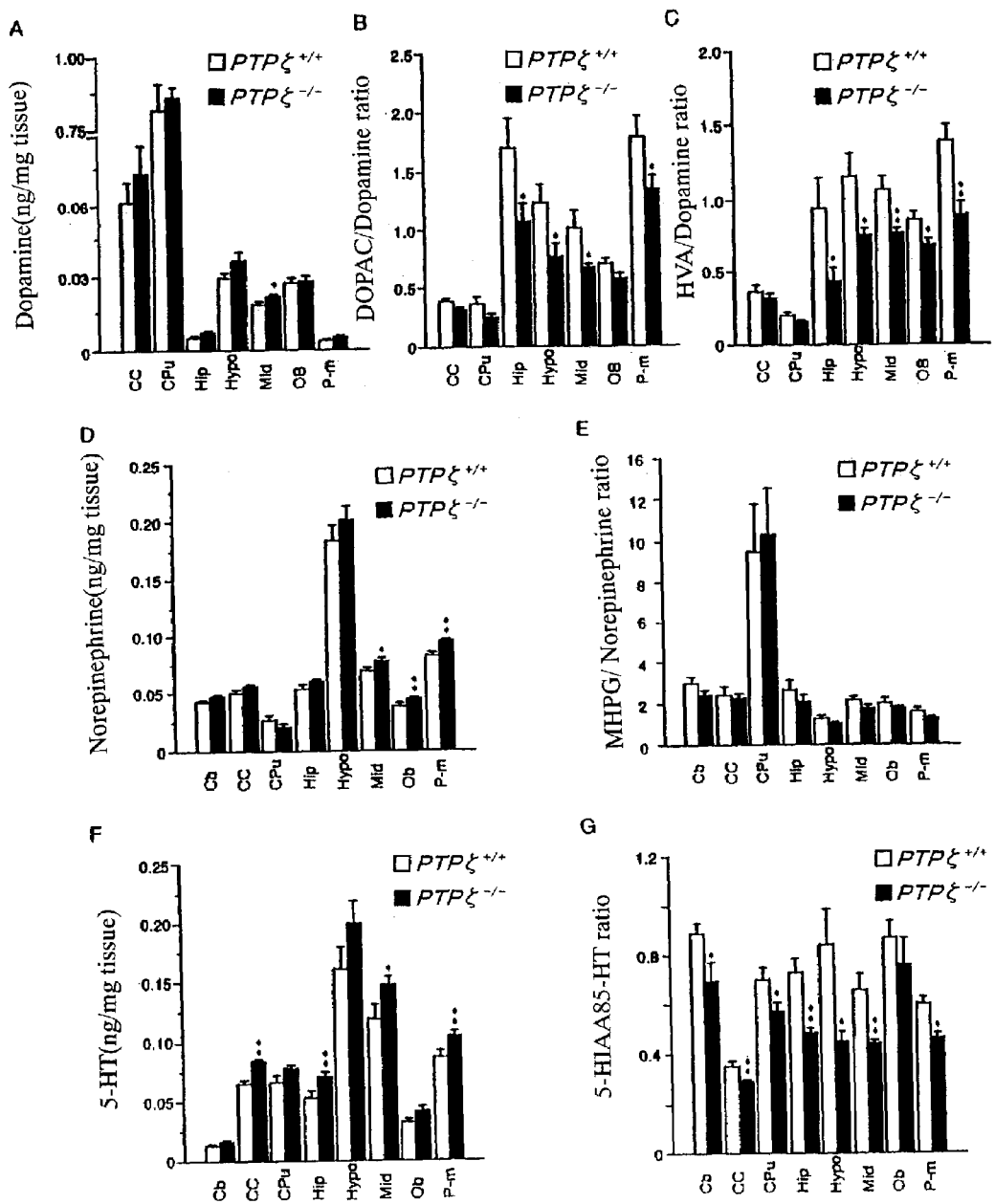
FIG. 2 is a view showing the changes of monoamine metabolism in the brains of PTPζ-deficient mice.

It has been known that locomotor activity and circadian rhythm are deeply linked to monoaminergic systems in the brain. Therefore, tissue contents of dopamine (DA), norepinephrine (NE), serotonin (5-HT) and their metabolites (DOPAC, HVA, metabolites of DA; MHPG, a metabolite of NE; 5-HIAA, a metabolite of 5-HT) in the brains were measured by high-performance liquid chromatography (HPLC) and an electrochemical detector (ECD) (the above-mentioned method A-4-1). The results are shown in FIG. 2. The data are presented as mean±SEM from PTPζ$^{+/+}$ mice (n=7) and PTPζ$^{-/-}$ mice (n=7) (*$p<0.05$, **$p<0.01$). As a result, metabolism of monoamine in the brains of the PTPζ-deficient mice was revealed to be apparently abnormal. There was almost no difference between the two genotypes in the tissue content of DA (A). However, the ratios of DOPAC/DA (B) and HVA/DA (C), 5-HIAA/5-HT (G) in several brain regions of the PTPζ-deficient mice were markedly decreased compared to those of the wild-type mice. The content of NE in the PTPζ-deficient mice increased compared to that of the wild-type mice.

(Immunohistological Analysis of DA Pathway)

Figure 3:
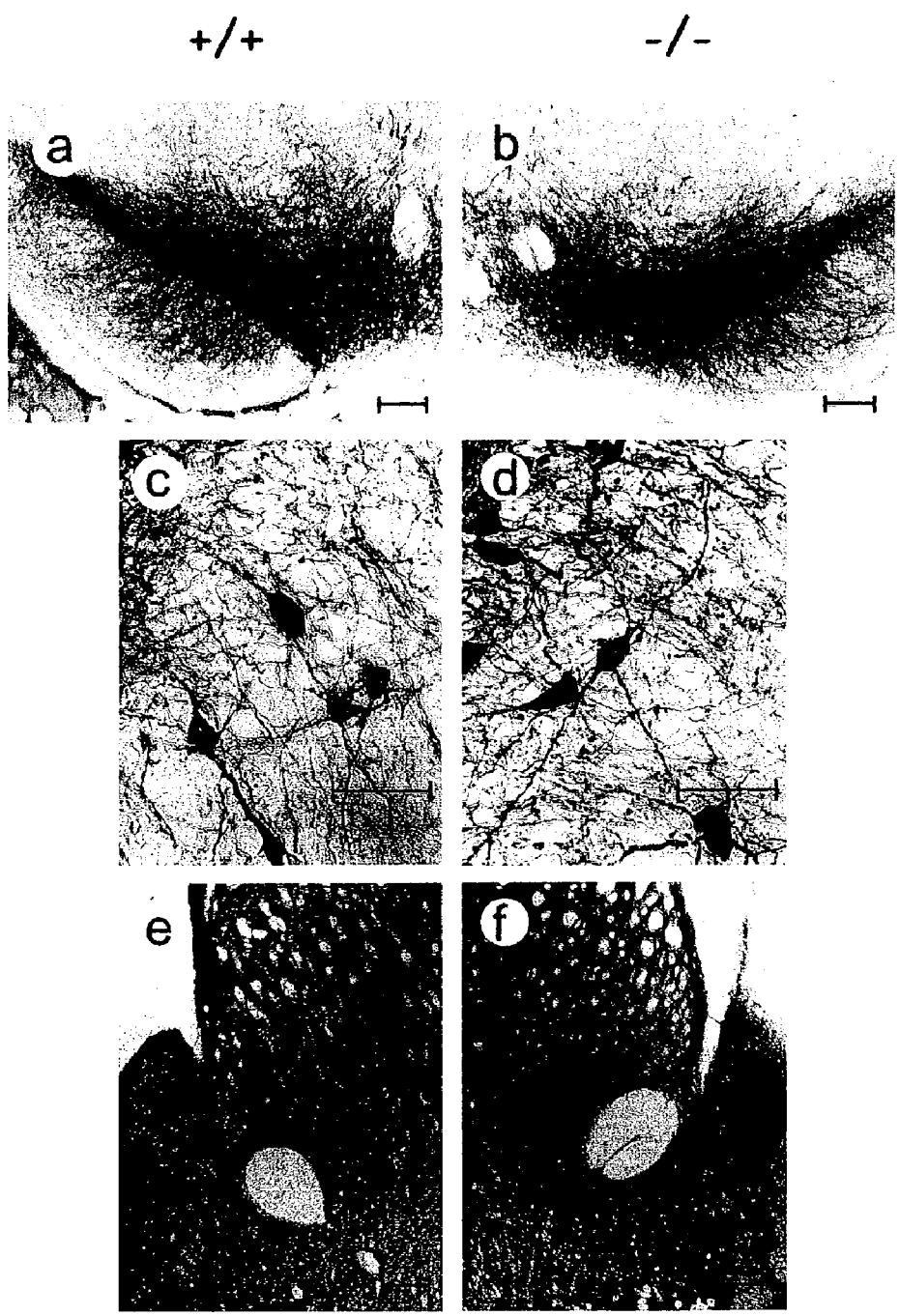
FIG. 3 is a view showing the examination results of immunohistochemistry of dopamine pathway in PTPζ-deficient mice.

Next, DA pathway of PTPζ-deficient mice was analyzed immunohistologically for detecting the presence of histological change therein with a specific antibody to tyrosine hydroxylase, a marker enzyme of DA neurons (the method A-5). The results are shown in FIG. 3. Regions of wild-type mice (+/+, left side) and PTPζ-deficient mice (−/−, right side) through the substantia nigra and ventral tegmental area (low-magnification photographs, a and b; and high-magnification photographs, c and d), and striatum (e and f) were analyzed immunohistochemically with polyclonal antibodies specific to tyrosine hydroxylase (TH). According to the results, no significant difference was identified between DA pathways of the PTPζ-deficient mice and the wild-type mice, and DA pathway was considered to remain immunohistologically normal after PTPζ became deficient. The scale bars, 500 μm (a, b, e, and f), and 50 μm (c and d).

(Decrease in Sensitivity to Stimulant Drugs)

Figure 4:
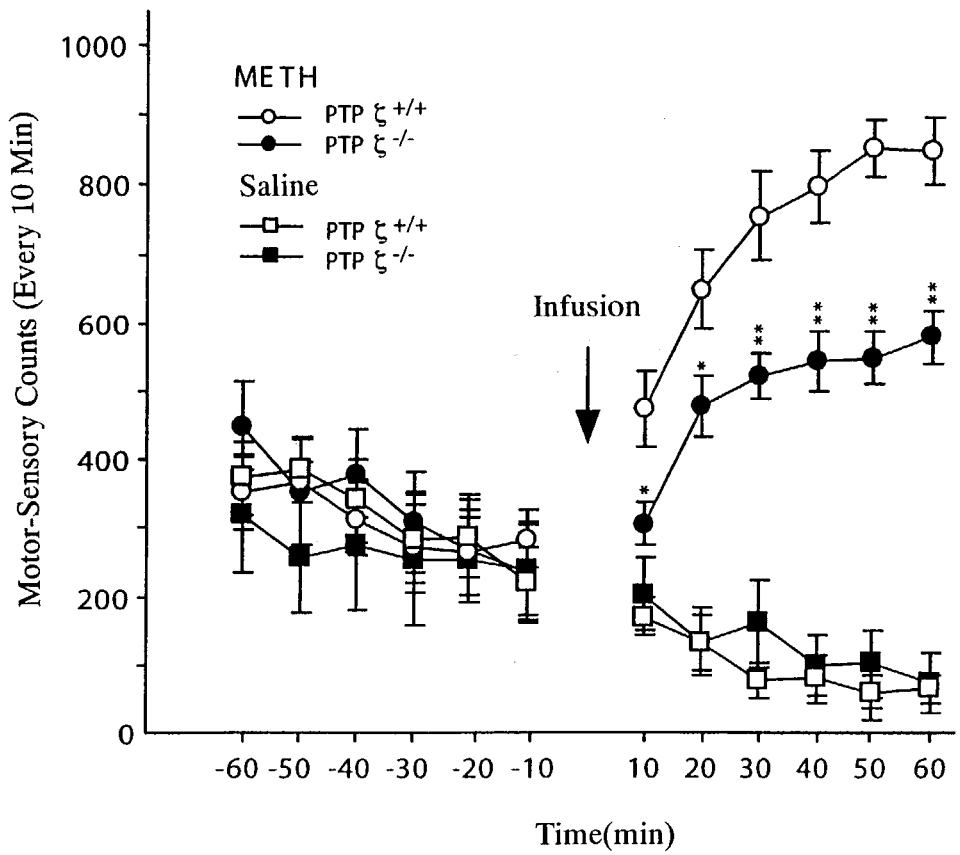
FIG. 4 is a view showing the decrease of locomotor activity to methamphetamine and GBR 129909 in PTPζ-deficient mice.
Figure 4:
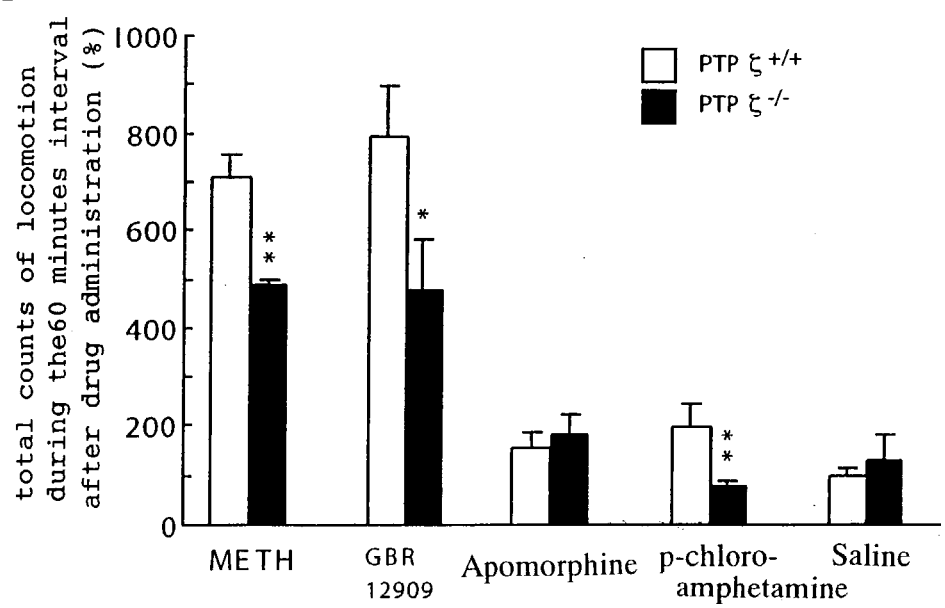

Methamphetamine (METH), a stimulant drug, acts on DA pathway and increases the locomotion of mice markedly. In expectation of a possibility of functional change in DA pathway of PTPζ-deficient mice, sensitivity to METH was analyzed by an electromagnetic locomotion measuring apparatus (the above-mentioned method A-3). The results are shown in FIG. 4. Mice were placed in an acrylic chamber, and locomotion was measured by the counts of electromagnetic sensors. PTPζ$^{-/-}$ mice (n=9) and PTPζ$^{+/+}$ mice (n=9) showed similar time course of locomotor activity before drug administrations. After an adequate acclimation (at least 90 minutes), methamphetamine (METH, 1 mg/kg, s. c.) or saline (arrow point) was injected, and it was indicated that the PTPζ$^{-/-}$ mice exhibited a significantly attenuated locomotor response compared to the wild-type mice (FIG. 4A). No change was observed in the control group administered with saline. The data are presented as mean±SEM per each 20 minutes interval (p<0.001 for phenotype).

Effects of METH (1 mg/kg, s. c.), GBR12909 (2 mg/kg, i. p.), apomorphine (2 mg/kg, s. c.), p-chloro-amphetamine (2 mg/kg, i. p.) and saline on locomotor activity are presented in FIG. 4B as the total counts of locomotion during the 60 minutes interval after drug administration. Locomotor activity was measured in the same manner as above-mentioned. The data are presented as mean±SEM (*p<0.05, **p<0.01). PTPζ-deficient mice showed similar hyposensitivity also to GBR12909, a specific inhibitor of DAT (FIG. 4B). On the other hand, though apomorphine, a non-specific agonist for DA receptors, shows similar effect by stimulating a postsynaptic neuron, responsiveness to apomorphine was normal (FIG. 4B). These results suggest that neurotransmitting function of a presynaptic neuron is abnormal in DA pathway of the PTPζ-deficient mice. The PTPζ-deficient mice were hyposensitive also to p-chloro-amphetamine that liberates 5-HT from a presynaptic region (FIG. 4B).

[$^3$H] DA was mixed with striatal synaptosomes and [$^3$H] DA uptake into tissues was measured (the above-mentioned method A-6-1). The homogenate of the striatal synaptosomes was incubated for 2 minutes at 30.degree. C. in the presence of [$^3$H] DA (1 to 10 nM). The amount of DA uptake was analyzed by Eadie-Hofstee plot, and maximum velocity (Vmax, pmol/2 min/mg protein) and affinity (Km, nM) are presented in Table 1, as mean±SEM of three measurement values (*P<0.05). From Table 1, it was found that both of maximum velocity (Vmax) and affinity (Km) of DA uptake amount are changed dynamically, though there was no difference in the number of DAT.

TABLE 1

| Mice | [$^3$H] DA uptake | |
|---|---|---|
| | Km (nM) | Vmax (pmol/3 min/mg) |
| PTPζ$^{+/+}$ | 109.2 ± 2.45 | 45.74 ± 2.77 |
| PTPζ$^{-/-}$ | 147.3 ± 11.3 | 58.70 ± 1.03 |

(Abnormality of DA Neurotransmission in Nucleus Accumbens)

Figure 5:
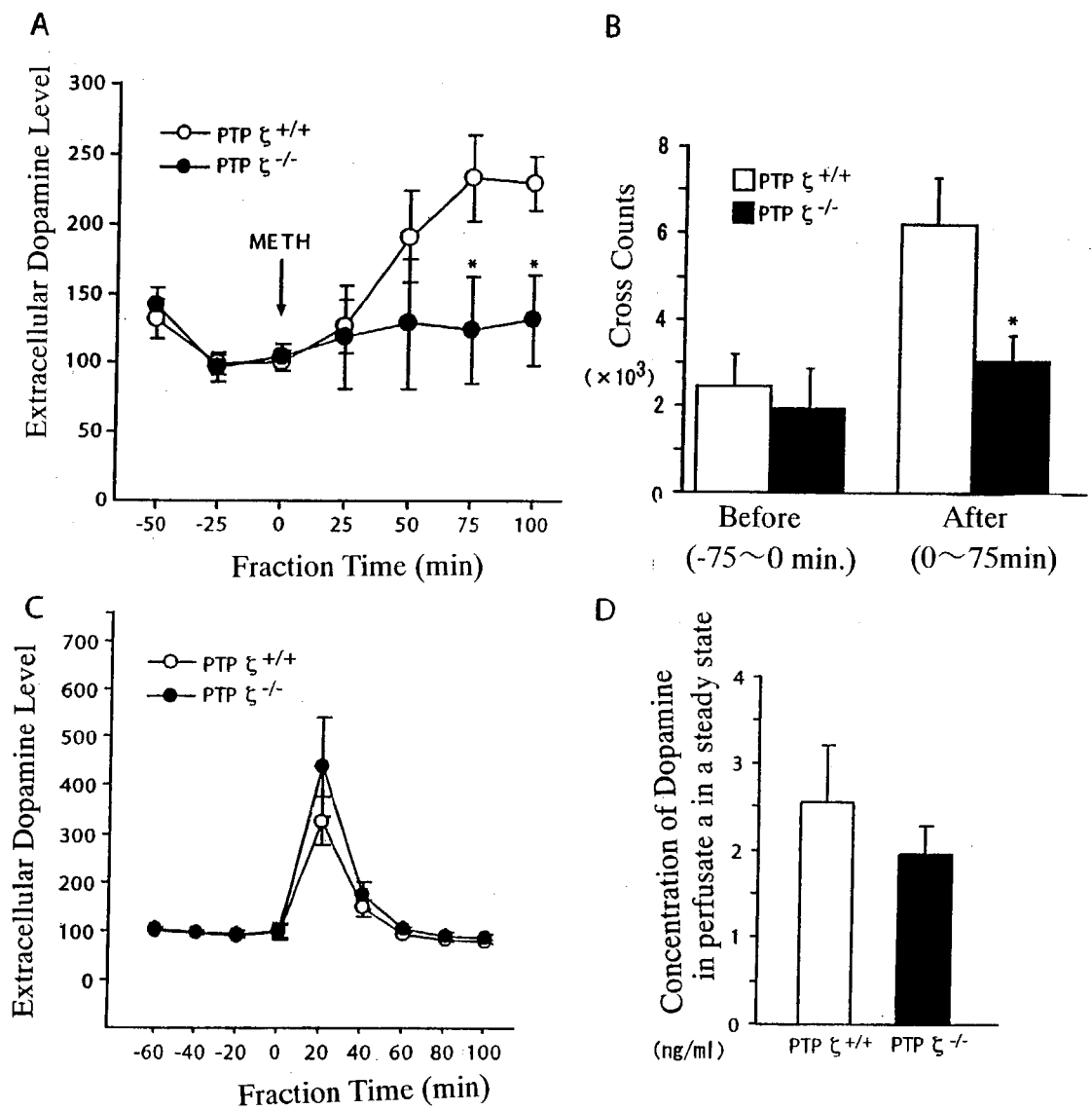
FIG. 5 is a view showing the abnormal DA neurotransmission in nucleus accumbens of PTPζ-deficient mice.

Effect of activating locomotor activity caused by administration of METH or GBR12909 is induced mainly by an increase of extracellular DA concentration in nucleus accumbens (NAC). The change of extracellular DA concentration in nucleus accumbens after the administration of METH was analyzed by microdialysis (the above-mentioned method A-4-2). METH-induced DA release in the NAC was analyzed by microdialysis, and the results are shown in FIG. 5A. Each value is mean±SEM from PTPζ$^{+/+}$ mice (n=7) and PTPζ$^{-/-}$ mice (n=6), and the precentage value to the average of 2 samples before METH stimulation. The PTPζ-deficient mice exhibited a markedly diminished DA release evoked by administration of METH (1 mg/kg, s. c.) compared to the wild-type mice (P<0.001 for phenotype). In the wild-type mice, the extracellular DA in nucleus accumbens definitely increased by the administration of METH (1 mg/kg, s. c.), on the contrary, in the PTPζ-deficient mice, extracellular DA increasing response evoked by METH stimulation attenuated obviously in comparison to that of the wild-type mice (FIG. 5A).

It was confirmed that locomotor activity after METH administration attenuated in PTPζ-deficient mice corresponding to the extracellular DA concentration. Locomotion of freely moving animals was analyzed by an infrared monitoring apparatus, confirming that PTPζ$^{-/-}$ mice exhibited a statistically attenuated METH-enhanced locomotion after METH stimulation compared to wild-type mice (*p<0.05). The results are shown in FIG. 5B. In other words, it was identified that the cause of hyporesponsiveness to stimulant drugs was presented in the process of release and uptake of DA from a presynaptic region. On the other hand, when DA releases from synaptic vesicles were induced by causing depolarization by local administration of 100 mM KCl solution through microdialysis probe inserted into the nucleus accumbens, DA release response of PTPζ-deficient mice was the same level as that of wild-type mice (FIG. 5C). In addition, as there was no change in the extracellular DA concentration in a steady state as well (FIG. 5D), it was revealed that PTPζ was not essential to the release mechanism of DA synaptic vesicle.

(Role of PTPζ in DA Pathway)

Figure 6:
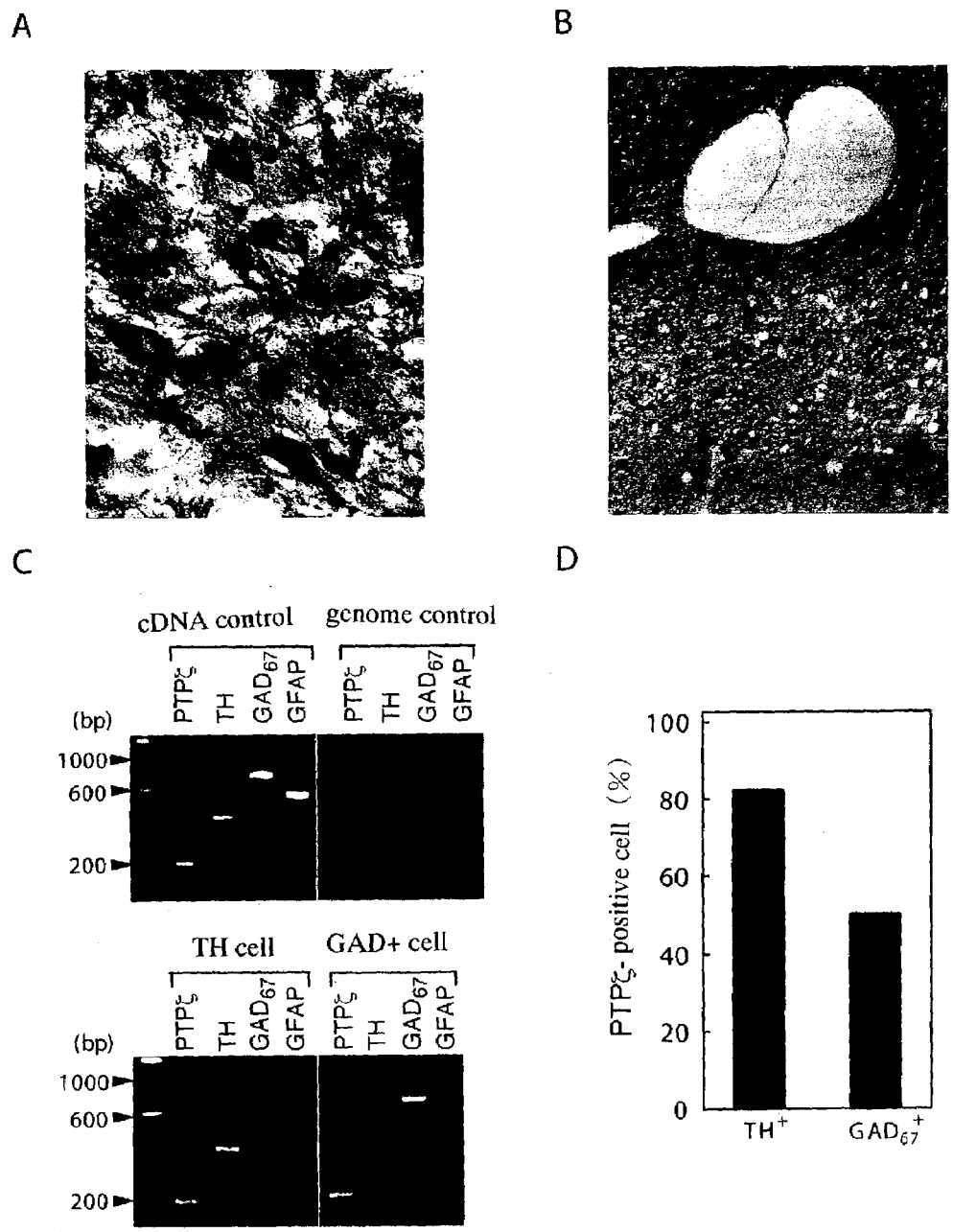
FIG. 6 is a view showing the examination results of expression property of PTPζ in dopamine pathway of adult mice brains.

It is very important to clarify the region of PTPζ expression in elucidation of the role of PTPζ in DA pathway. As detailed expression pattern of PTPζ in mature brain is unknown, the expression region of the molecule was identified from the expression pattern of a LacZ gene, a reporter gene of the PTPζ gene, in this case. In other words, cells that were stained blue by X-gal were identified as PTPζ-positive cells. Regional distribution of cells that display PTPζ promoter activity in the DA circuit of adult mice was examined in adult heterozygous mice by X-gal staining (blue signal), and then by TH staining (brown signal), and the results are shown in FIGS. 6A and B. A number of positive cells were observed in substantia nigra (SN) and ventral tegmental area (VTA), which are nuclei of origin of DA pathway,on the contrary, no cells were detected in striatum (ST) and nucleus accumbens (NAC), which are the main regions for receiving DA projections. This result is consistent with the result of pharmacological analysis wherein the functional change in the presynaptic region of DA pathway was identified by deficiency in PTPζ.

Next, in order to confirm a possibility that PTPζ functions directly in DA neurons, an analysis by RT-PCR using RNA prepared from single cells as a template, that is, single-cell RT-PCR, was conducted (the above-mentioned method A-7 and A-8). Single-cell RT-PCR using cDNA derived from mouse brain as a template was conducted, then the products were analyzed by agarose gel electrophoresis, followed by ethidium bromide staining, and the results are shown in the top of FIG. 6C. Phosphatase domain D1 of PTPζ and PCR products of a marker gene, tyrosine hydroxylase (TH, dopamine neuron marker), glutamic acid decarboxylase (GAD67, GABA neuron marker) and glial fibrary acidic protein (GFAP, astroglia cell marker) were detected in each position expected from its mRNA base sequence, that is, PTPζ (189), TH (377), GAD67 (702), GFAP (517). The validity of these PCR products were verified by DNA sequencing after cloning. PCR amplification from genomic DNA did not occur because primers were set to sandwich an intron therebetween. In addition, PCR amplification was not observed in controls to which no reverse transcriptase was added. Representative examples being identified as TH-positive (DA neurons) and GAD-positive (GABA neurons) are shown at the bottom of FIG. 6C. As a result that 46 cells were collected from substantia nigra and ventral tegmental area of 4 mice and analyzed, 28 of TH-positive dopamine neurons and 6 of GAD67-positive GABA neurons were identified. Eight cells that amplified neither TH nor GAD, and 4 cells wherein amplification of GFAP was observed were excluded from the analysis. Amplification of PCR products of PTPζ was observed in 83% of DA cells (FIG. 6D). In other words, it was proved that receptor-type PTPζ having protein tyrosine dephosphorylating activity was expressed in most DA neurons in brains of adult mice.

(Change in Responsiveness to Forced Swimming Stress)

Figure 7:
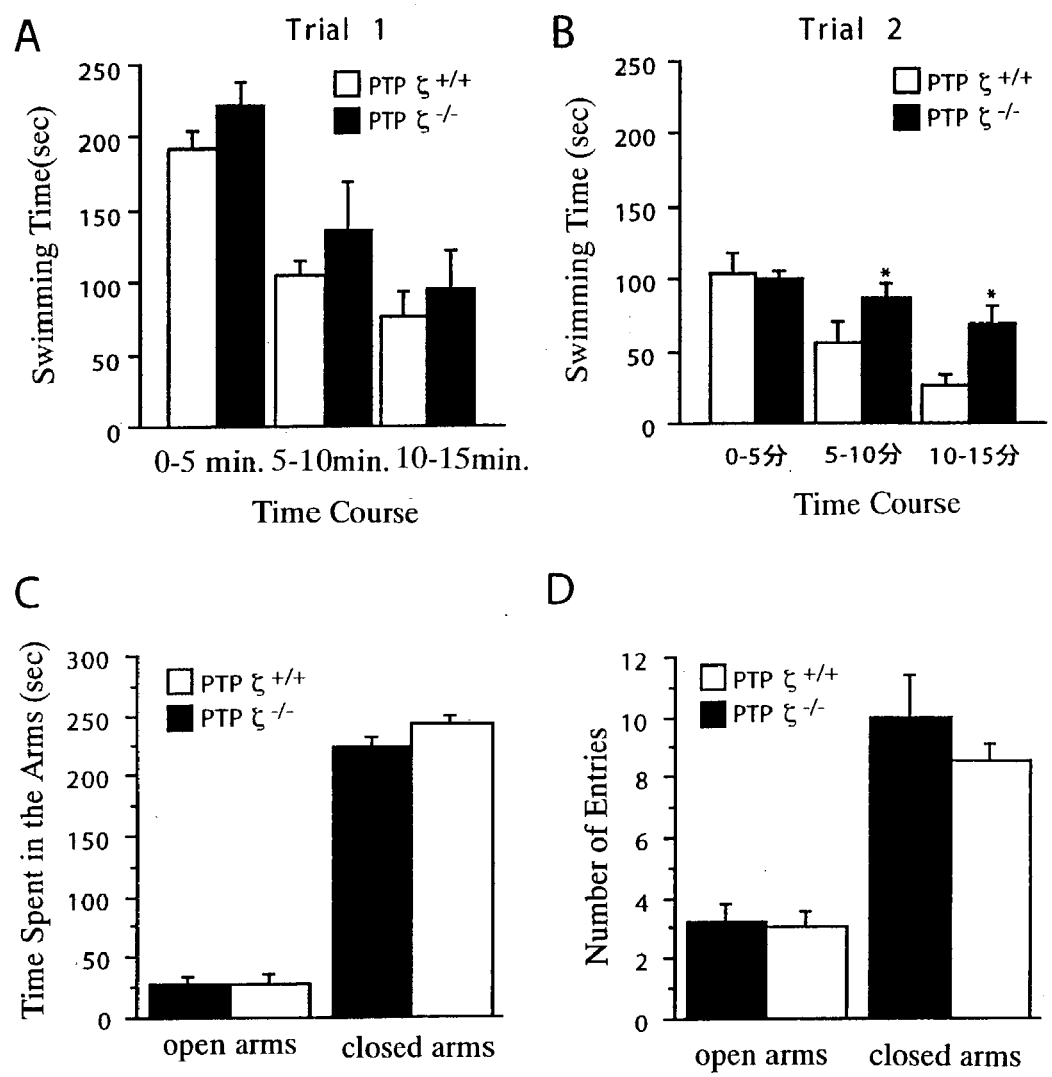
FIG. 7 is a view showing the results of stress and fear behaviors in PTPζ-deficient mice.

It is known that DA and 5-HT pathways are involved not only in locomotor activity but also in emotion and stress response. In a forced swimming stress test, mice were placed into a narrow pool under inescapable condition, and the swimming time was evaluated/analyzed in time course (the above-mentioned method A-2-3). It is presumed that though animals actively swim to escape from stress stimulus at first, they despair of inescapable situation and gradually become less mobile. A 15 minutes' test on the first day was conducted to induce a state of depression. In this test, there was no significant difference between the swimming time of deficient mice and wild-type mice (FIG. 7A). However, in a test conducted 24 hours later, it was shown that the PTPζ-deficient mice swam longer than the wild-type mice (FIG. 7B). During the 15 minutes' test, mouse locomotion gradually decreased, and the activity level during the last 10 minutes was significantly greater in the PTPζ-deficient mice (n=8) than in the wild-type controls (n=8). That is, it was found that the PTPζ-deficient mice were hard to be acclimated to stress stimulus.

An elevated plus maze test, which is a general method for evaluating emotional behaviors, anxiety in particular, was conducted next (the aforementioned method A-2-4). In this test, mice are subjected to ambivalent condition wherein they try to avoid the open arms of maze because brightness makes them anxious, while they feel like exploring the site at the same time. In other words, animals that are susceptible to anxiety will avoid the open arms and spend longer time in the closed arms. On the other hand, mice having a strong desire to exploration will show more exploration behavior and in and out movement between the open and the closed arms. There was no apparent difference between PTPζ-deficient mice (n=9) and wild-type controls (n=12) in their behaviors in the elevated plus maze (FIG. 7C). Further, as to the total number of entries into the arms of the maze, which is a measured value of exploration behavior, no difference was observed between the two phenotypes as well (FIG. 7D). The two kinds of mice were evaluated as comparable in these two factors, time spent in the open-the close arms (anxiety behavior) and the total number of entries into the arms (exploration behavior).

(Change in Exploration Behavior to a Novel Object)

Figure 8:
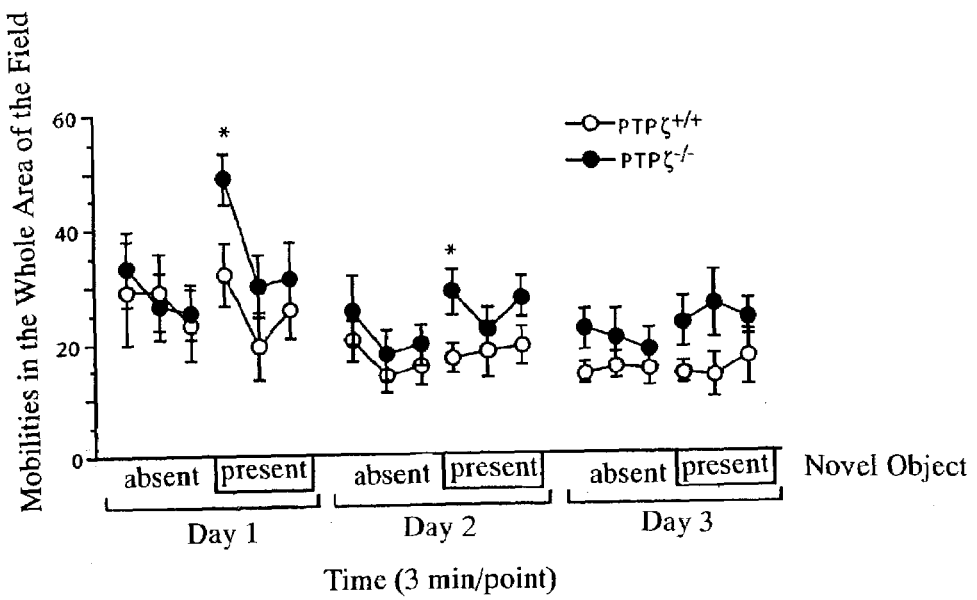
FIG. 8 is a view showing the results of exploration behavior of wild-type mice and PTPζ-deficient mice to a novel object.
Figure 8:
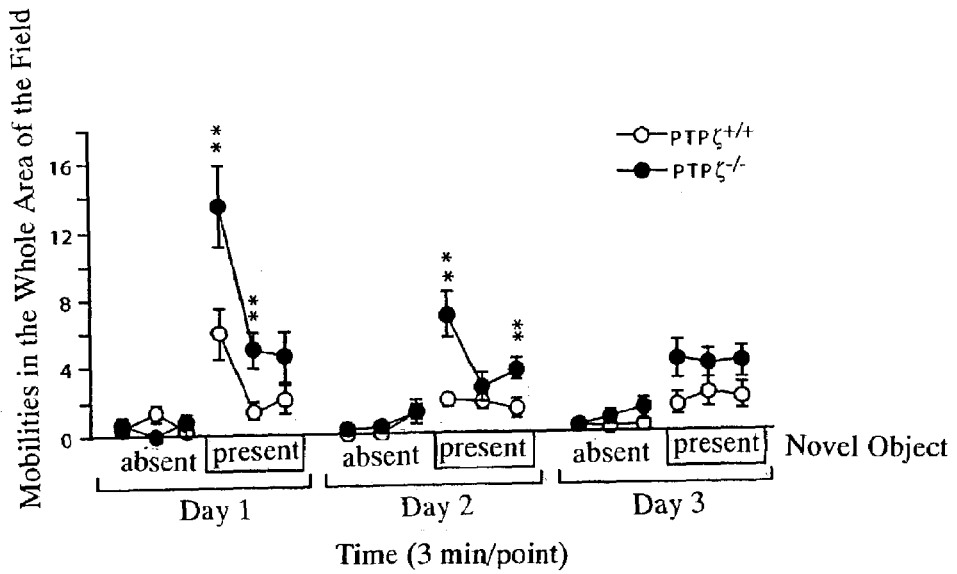

Exploration behaviors to an object never seen before was examined (the above-mentioned method A-2-5). The results are shown in FIG. 8. Mobilities of PTPζ-deficient mice (PTPζ$^{-/-}$, n=9) and wild-type controls (PTPζ$^{+/+}$, n=9) in the whole area of the open field (FIG. 8A) and the central area of the open field (FIG. 8B) are presented as mean±SEM per each 3 minutes ($*p<0.05$, $**p<0.01$). At the first measurement (Trial. 1), nothing was placed in the field during the first 9 minutes. It was found that both types of mice hardly stayed in the central area in this circumstance. Subsequently, when a block (an object never seen before) was placed at the center of the field, mice showed exploration behavior to the block, and remarkably increased the frequency of going in and out of the central area. In accordance with this increase, overall mobility also increased. Further, the graph showed the time course decrease of exploration behaviors to the block. When comparing the two types of mice, PTPζ$^{-/-}$ mice showed mobility twice or more higher than that of wild-type mice during the first 3 minutes in the central area where the block was placed, and kept showing significantly higher mobility until the first 6 minutes passed. 24 hours later, the second trial (Trial. 2) was conducted under the same condition. Mobility of wild-type mice (PTPζ$^{+/+}$) showed almost no increase, consequently, it was considered that the mice stopped exploring the block, on the other hand, PTPζ$^{-/-}$ mice showed an increase in mobility which was considered to be caused by exploration behavior as before. When the third trial (Trial. 3) was conducted, significant difference between the two types of mice was no longer observed. These results indicate that PTPζ$^{-/-}$ mice are slow in acclimating to a new circumstance.

EXAMPLE 2

(Role of PTPζ in Gastric Ulcer Formation Caused by VacA, a Toxin of *Helicobacter pylori*)

The role of PTPζ in gastric ulcer formation caused by *Helicobacter pylori*, in particular, immunohistological identification of PTPζ in stomach, actual involvement of PTPζ as a receptor of exotoxin VacA secreted by *Helicobacter pylori* in gastric ulcer formation, and the usefulness of a PTPζ-deficient mouse as a negative control were considered.

EXAMPLE 2-1

[Method]

(B-1 Immunohistochemical Staining of PTPζ in Mouse Stomachs)

Formalin-fixed and paraffin-embedded stomach tissue sections of wild-type and PTPζ-deficient mice were immu nostained with anti-6B4 proteoglycan polyclonal antibody that recognizes the extracellular region of PTPζ. The tissue sections were deparaffinized in xylene, and dehydrated in ethanol. The sections were washed with phosphate buffered saline (PBS, pH 7.6), then subjected to microwave for 15 minutes in 10 mM citrate buffer (pH 6.0). The deparaffinized sections were incubated for 10 minutes with 0.3% hydrogen peroxide, and washed with PBS after blocking endogenous peroxidase. Subsequently, the sections were blocked with bovine serum albumin for 10 minutes, and washed with PBS. The treated tissue sections were incubated overnight with anti-6B4 proteoglycan polyclonal antibody (1:2000) in Tris-HCl buffer at 4.degree. C. containing a carrier protein and 15 mM sodium azide. After the sections were washed with PBS, their specific antibody binding was examined by DAKO Envision System (DAKO Corp.) by using DAB and $H_2O_2$ as substrates in accordance with manufacturer's protocol. The sections were slightly counter stained with hematoxylin.

(B-2 RT-PCR and Western Blotting of PTPζ in Mouse Stomachs)

RT-PCR of PTPζ in mouse stomachs was conducted as follows. TRIzol Reagent (Invitrogen) was used for extracting RNA from mouse stomach tissues. TrueScriptII Reverse Transcriptase kit (Sawady Technology Co., Ltd.) and oligo dT primer (dT) 30 were used for synthesizing cDNA. PCR was performed with 10 ng cDNA derived from RNA as a template, 10 pmol of primer, 0.5 U of EX-Taq polymerase (Takara Shuzo) and reaction buffers attached to EX-Taq polymerase, in a total volume of 20 μl. The PCR was conducted under the following conditions: one cycle at 94.degree. C. for 5 minutes, 35 cycles at 95.degree. C. for 30 seconds, 62.degree. C. for 3 seconds, 72.degree. C. for 2 minutes, and finally one cycle at 72.degree. C. for 5 minutes. In addition, the validity of the sequences of PCR amplification products were confirmed by examining DNA sequences. PCR domains corresponding to each isoform of PTPζ are PTPζ-A type (nucleotide No. 4861-5499), PTPζ-B type (2321-2875), and PTPζ-S type (4913-5704).

Western blotting for detecting PTPζ in mouse stomachs was conducted as follows. With Tris buffer containing 1% NP-40 and protease inhibitors, gastric tissues were homogenized, and after the supernatant was obtained by centrifugation. Chondroitinase ABC treatment of the supernatant was carried out at 37.degree. C. for 1 hour. Further, proteins were separated by SDS-PAGE (6% acrylamide gel) and transferred to PVDF membrane by semi-dry transfer. In addition, rabbit anti-6B4 polyclonal antibody (1 μg/ml) and peroxidase-labeled anti-rabbit antibody were used as secondary antibodies for immunostaining to detect PTPζ. As a reaction substrate, ECL Plus reagent (Amersham Pharmacia) was used.

(B-3 Formation of Gastric Ulcer Caused by VacA, a Toxin of *Helicobacter pylori*)

After a mouse (female) of 4 weeks old was starved for 24 hours (fed water ad libitum), VacA, a toxin of *Helicobacter pylori* or saline was orally administered to the mouse with a sound. 48 hours later, gastric specimens were prepared and the surface of inside wall of stomach was observed by a stereomicroscope, and then pathologic specimens were prepared by hematoxylen eosin staining and analyzed.

(B-4 Pathological Evaluation of Gastric Ulcer Formation Caused by VacA)

Pathological evaluation of gastric ulcer formation caused by VacA was conducted in a following way. Epithelial damage score (EDS) was estimated according to the following scale: 1=no lesion; 2=disarray of columnar cells; 3=diffuse microerosions and epithelium disaggregation; 4=erosive lesion, denudation of basal membrane, and ulceration. At EDS level 4, gastric mucosal ulceration was considered to have occurred. For the inflammation score (IS), the amounts of inflammatory cells were graded as follows: 1=none; 2=scattered mononuclear and polymorphonuclear cells in the lamina propria and submucosa; 3=definite increase in subepithelial areas of lamina propria; 4=marked infiltration of lamina propria.

(B-5 Analyses of Phosphorylation Level of GIT1, a Substrate Molecule of PTPζ and Cell Vacuolation in AZ-521 Cells)

In order to analyze phosphorylation level of GIT1 (G protein-coupled receptor kinase-interactor 1) (PNAS, 98, 6593–6589, 2001), a substrate molecule of PTPζ, and cell vacuolation in AZ-521 cells, uptake of neutral red and immunoprecipitation were conducted as follows. First, AZ-521 (Health Science Research Resources Bank), a cancerous cell strain derived from human stomach hypersensitive to VacA, was inoculated on a plate such that cell density was adjusted to be 350,000/cm$^2$ and cultured for 24 hours, and then added with acid-activated VacA and 100 ng/ml EGF. 30 minutes after the stimulation, cell vacuolation (uptake of neutral red) and tyrosine phosphorylation level of GIT1 (immunoprecipitation) were analyzed.

An uptake test of the pigment, neutral red, was conducted as follows. After components of the medium were removed, phosphate buffer containing 0.05% neutral red and 0.5% BSA was added and made the cells uptake it for 5 minutes. The cells were washed three times with phosphate buffer containing 0.5% BSA and then the intracellulary uptaken pigment was extracted with 70% ethanol containing 0.05% hydrochloric acid, and absorbance (540 nM) was measured.

Next, a tyrosine phosphorylation test of GIT1 was conducted as follows. 300 μl of lysis buffer (20 mM Tris-HCl, pH 8.0, 137 mM NaCl, 1% NP-40, 1 mM phenylmethylsulfonyl fluoride, 10 μg/ml pepstatin A, 1 mM sodium orthovanadate, and 1 mM NaF) was added to 1.9×10$^6$ cells and the resulting mixture was left on ice for 30 minutes. After centrifuging the extract of the mixture, protein concentration of the supernatant was adjusted to be 100 μg/ml. 25 μg sample and 25 μl Protein G Sepharose 4FF (Amersham Pharmacia) were mixed for 2 hours, and the supernatant wherein components nonspecifically adsorbing to gel was excluded was prepared. 2 μl of rabbit anti-GIT1 antiserum was added to the supernatant, and 1 hour after the reaction, 25 μl Protein G Sepharose 4FF was added and Reaction was conducted for another 3 hours. After the reaction, beads were washed three times with lysis buffer, and then specifically adsorbing components were extracted with sample buffer of SDS-PAGE. This sample was separated by SDS-PAGE and subsequently transferred to PVDF membrane by semi-dry transfer, and used for immunoprecipitation. Anti-tyrosine phosphorylation mouse monoclonal antibody PY20 was used for the detection of tyrosine phosphorylation of GIT1 and goat anti-GIT1 antibody (Santa Cruz Biotechnology, Santa Cruz) was used for the detection of GIT1.

EXAMPLE 2-2

[Results]

(Expression of PTPζ in a Mouse Gastric Epithelial Cell Layer)

Figure 9:
FIG. 9 is a view showing the examination results of PTPζ expression in gastric epithelial cell layer of wild-type mice and PTPζ-deficient mice.
Figure 9:

Whether PTPζ was expressed in the mouse gastric epithelial cell layer was examined by using rabbit polyclonal antibody which specifically recognizes the extracellular domain of PTPζ, and the results are shown in FIG. 9 (see reference 3). As it can be seen from the wild-type mouse (FIG. 9A) and the PTPζ-deficient mouse (FIG. 9B), it has been revealed for the first time that PTPζ expresses in a gastric epithelial cell layer of a wild-type mouse. The reason why PTPζ was originally thought to express only in central nervous system may be explained by the fact that the expression in stomach was too low in comparison to that in brain to be distinguished from the background. In the present invention, it was possible to set extremely hypersensitive immunostaining conditions as a result of the use of PTPζ-deficient mice as negative controls.

(Expression of PTPζ Isoforms in a Mouse Gastric Epithelial Cell Layer)

Figure 10:
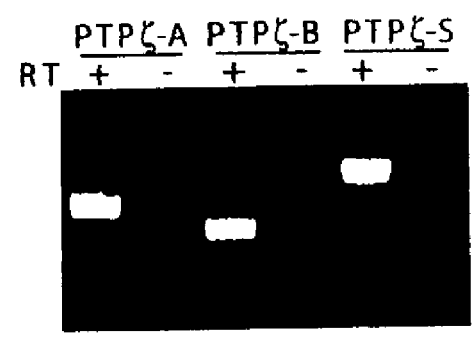
FIG. 10 is a view showing the examination results of transcription (RT-PCR) and expression (Western blot) of PTPζ in gastric epithelial cell layer of mice.
Figure 10:
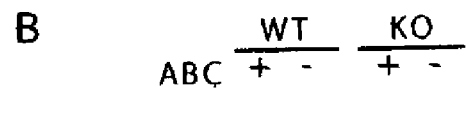

The result of RT-PCR confirmed the expression of all splice variants of PTPζ-A type, PTPζ-B type and PTPζ-S type in gastric tissue (FIG. 10A). On the other hand, Western blot analysis indicated that receptor-type PTPζ-B type was dominant as an actual protein component, and as eletrophoretic mobility was not changed by chondroitinase ABC treatment, it was revealed that the PTPζ-B type expressed in the stomach is not modified with chondroitin sulfate (FIG. 10B).

(Formation of Ulcer in Mouse Gastric Epidermis)

Figure 11:
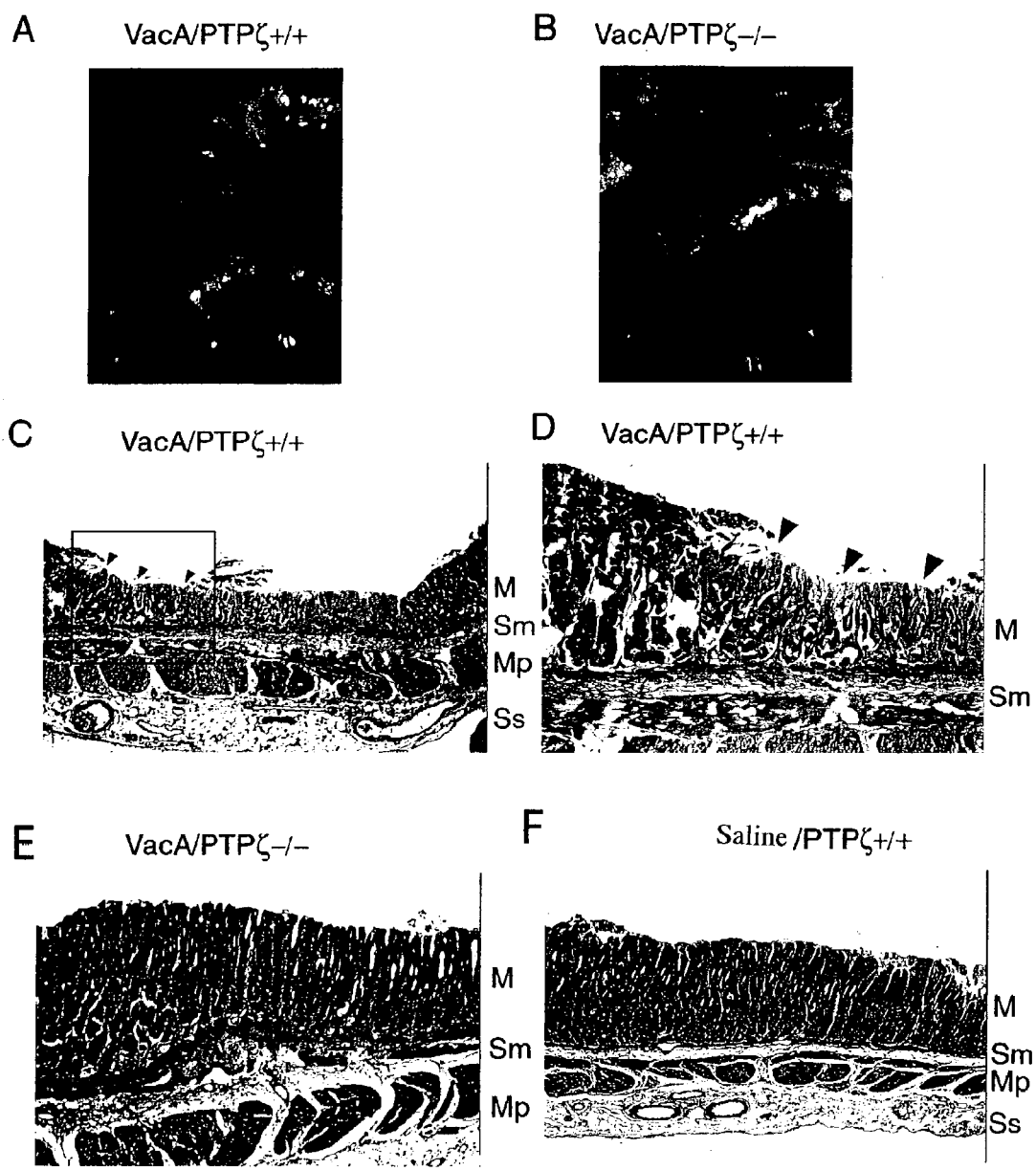
FIG. 11 is a view showing the results of gastric ulcer formation in wild-type mice and PTPζ-deficient mice orally administered with VacA, a toxin of *Helicobacter pylori*.

Formation of ulcer in mouse gastric epidermis at 48 hours after the administration of VacA was examined with a stereomicroscope. The results are shown in FIG. 11. As to wild-type mice that were administered with VacA, 3 out of 7 mice developed apparent ulcers in their stomachs (arrows, FIG. 11A), and in the stomachs of the other 4 mice, though it was not severe, formation of erosion or apparent disquamation of gastric epidermal layer was observed. On the contrary, in the stomachs of PTPζ-deficient mice (n=7) that were orally administered with VacA, no significant damage was observed (FIG. 11B). Hematoxylene eosine staining of specimens of wild-type mice administered with VacA showed representative ulcers (arrows in FIG. 11C with low magnification and in FIG. 11D with high magnification), and the appearance of the ulcer was found to closely resemble that of human lesions caused by an infection with *Helicobacter pylori*. By contrast, as the PTPζ-deficient mice were totally normal (FIG. 11E), it has been revealed for the first time at individual level that PTPζ plays an indispensable role in the formation of ulcer caused by VacA. As to groups to which saline was administered, both wild-type (FIG. 11F) and PTPζ-deficient mice were normal.

(Pathological Evaluation of Ulcer Formation on Mouse Gastric Epidermis)

The levels of epithelial damage score (EDS) and inflammation score (IS) were evaluated according to the method described in (B-4). Mean±SEM of EDS and IS are shown in Table 2. Epithelial damage and inflammation dependent to the dose of VacA were observed in wild-type mice (PTPζ+/+), but no abnormality was observed in PTPζ-deficient mice (PTPζ-/-). In the Table, the results of Mann-Whitney's U test comparing to wild-type mice administered with saline are shown as #, P<0.05: ##, P<0.001, and to wild-type mice administered with VacA (0.5 mg/kg) as **, P<0.001. Further, "nd" means that analysis was not conducted.

TABLE 2

| VacA (mg/kg) | n PTPζ+/+ | n PTPζ-/- | EDS PTPζ+/+ | EDS PTPζ-/- | IS PTPζ+/+ | IS PTPζ-/- |
|---|---|---|---|---|---|---|
| 0 | 7 | 7 | 1.1 ± 0.4 | 1.3 ± 0.5 | 1.3 ± 0.5 | 1.1 ± 0.4 |
| 0.125 | 5 | nd | 1.8 ± 0.8 | nd | 1.4 ± 0.9 | nd |
| 0.250 | 5 | nd | 2.2 ± 0.4# | nd | 1.4 ± 0.6 | nd |
| 0.500 | 10 | 10 | 3.8 ± 0.4## | 1.3 ± 0.5** | 3.6 ± 0.5## | 1.3 ± 0.5** |

(Analyses of Phosphorylation Level of GIT1, a Substrate Molecule of PTPζ and Cell Vacuolation in AZ-521 Cells)

Figure 12:
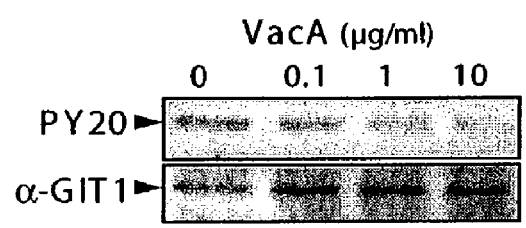
FIG. 12 is a view showing the examination results of tyrosine phosphorylation of GIT1, a substrate molecule of PTPζ, caused by stimulus with VacA.
Figure 12:
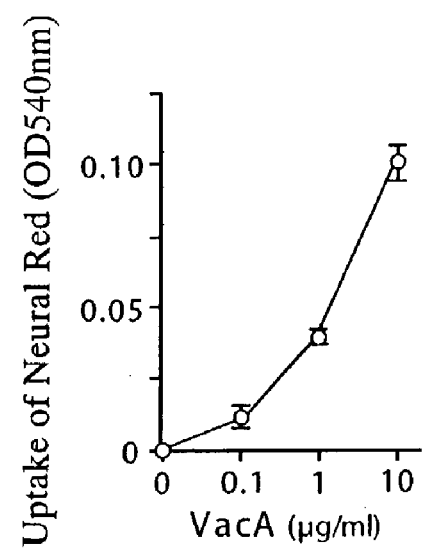

Tyrosine phosphorylation of GIT1, a substrate molecule of PTPζ, caused by stimuli with VacA was examined and the results are shown in FIG. 12. In VacA-hypersensitive strain AZ-521 cells, it was shown that tyrosine phosphorylation level of GIT1, a substrate molecule of PTPζ decreased dose-dependently by stimulation with VacA (FIG. 12A), and that decrease in phosphorylation of GIT1 was correlated with uptake of neutral red by cells (index of vacuole formation) (FIG. 12B). Cytotoxicity of VacA was evaluated as cell vacuolation ability in vitro, and a possibility that VacA is involved in vacuole formation by increasing the activity of PTPζ and by decreasing tyrosine phosphorylation of GIT1 has been shown.

EXAMPLE 3

(Role of PTPζ in Gastric Ulcer Formation Caused by Pleiotrophin)

Pleiotrophin is a heparin-binding secretory protein of 18 kD, and known to be involved in neurotrophic factor-like activity, adhesion of neurons, elongation of process and angiogenesis (BioScience Jargon Library: "Cytokine, Growth Factor", Yodosha, p126–127, 1998). Further, pleiotrophin is known to bind to extracellular regions of PTPζ (J. Biol. Chem. 271, 21446–21452, 1996) and alter the activity of PTPζ (PNAS, 97, 2603–2608, 2000). Therefore, whether pleiotrophin is involved in the formation of gastric ulcer was examined.

EXAMPLE 3-1

[Method]

The role of PTPζ in gastric ulcer formation caused by pleiotrophin was examined as follows. After a mouse (female) of 4 weeks old was starved for 24 hours (fed water ad libitum), pleiotrophin (Peptide Institute, Inc.) was orally administered to the mouse with a sound. 48 hours later, gastric specimens were prepared and the surface of inside wall of stomach was observed by a stereomicroscope, and then pathologic specimens were prepared by hematoxylen eosin staining and analyzed.

EXAMPLE 3-2

[Results]

Figure 13:
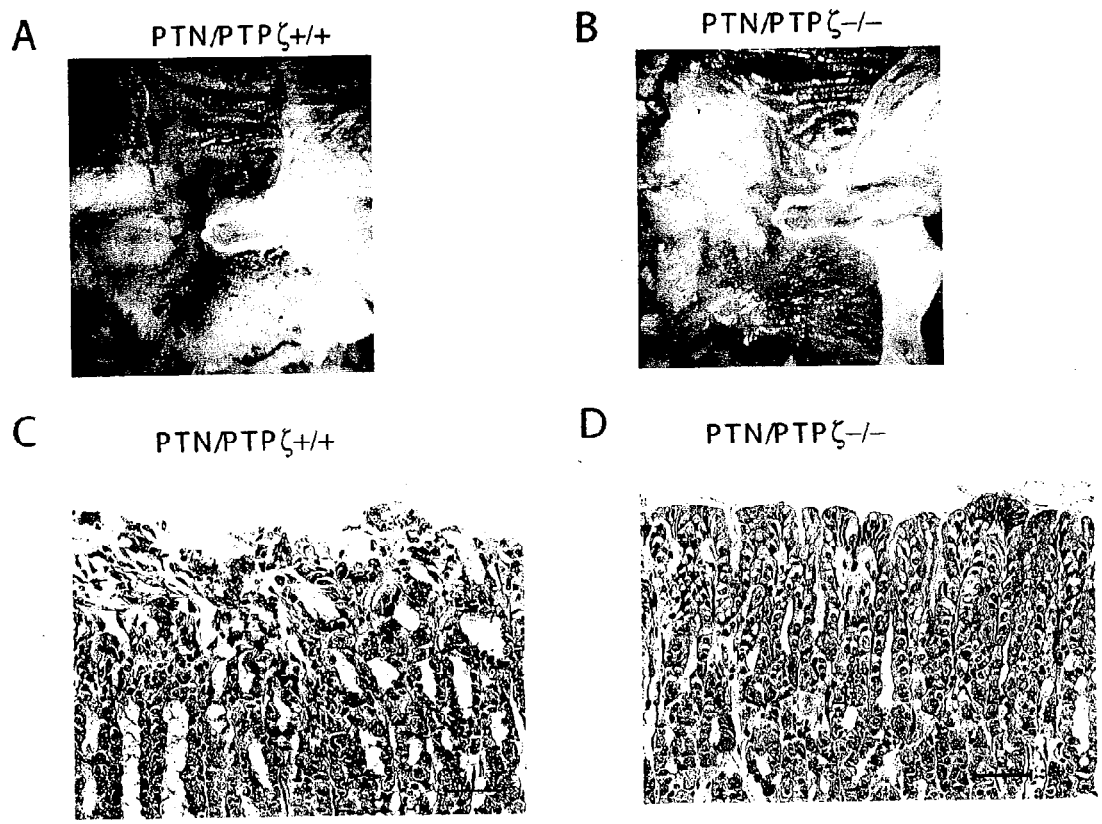
FIG. 13 is a view showing the results of mucosal damage in gastric epithelium of mice caused by administration of pleiotrophin.

The level of epithelial damage on mouse gastric epithelium at 48 hours after the administration of pleiotrophin was examined under a stereomicroscope. The results are shown in FIG. 13. Profuse bleeding was observed in stomachs of wild-type mice administered with pleiotrophin (FIG. 13A). By contrast, no damage was observed in stomachs of PTPζ$^{-/-}$ mice administered with pleiotrophin (FIG. 13B). As a result of hematoxylen eosin staining of specimens of wild-type mice administered with pleiotrophin, obvious damage was observed on gastric epithelium (FIG. 13C). On the other hand, PTPζ-deficient mice were totally normal (FIG. 13D) . These results revealed for the first time that ulcer was initiated by binding of PTPζ and a ligand molecule. The involvement of pleiotrophin in gastric ulcer formation is a finding that has never been known, and it was revealed that PTPζ-deficient mice were extremely useful as negative controls for the formation of gastric ulcer caused by pleiotrophin.

INDUSTRIAL APPLICABILITY

The present invention has shown for the first time that PTPζ is physiologically important in central monoamine pathway, particularly, in dopamine pathway. As pharmaceuticals that specifically adjust tyrosine phosphatase activity of PTPζ have not been developed yet, there is a good chance that screenings of specific pharmaceuticals with the use of PTPζ-deficient mice will lead to the development of a novel remedy for nervous affection.

Further, the present invention has histologically shown for the first time that PTPζ is actually expressed in stomach, and has demonstrated at the level of individual mouse that PTPζ is involved in the formation of gastric ulcer as a host receptor of VacA, a toxin secreted by *Helicobacter pylori*.

It is highly possible that these results will lead to the elucidation of onset mechanism of gastric ulcer caused by an infection with *Helicobacter pylori*, and the development of novel remedies for gastric ulcer and gastritis.

---

The invention claimed is:

1. A method for identifying a PTP-ζ inhibitor wherein a subject material is administered to a transgenic mouse whose genome comprises a homozygous disruption of the proteoglycan-type-receptor-type protein tyrosine phosphatase (PTP ζ) gene such that no PTP-ζ is expressed, wherein said mouse exhibits a dysfunction of the central monoamine pathway activity, and to a wild-type littermate mouse, and evaluating and comparing PTP ζ-related central monoamine pathway activities in the transgenic mouse and the wild-type mouse, wherein a decrease in central monoamine pathway activity in the wild-type mouse compared to that in the transgenic mouse is indicative of a subject material that is a PTP-ζ inhibitor.

2. The method for identifying a PTP-ζ inhibitor according to claim 1, wherein the comparison and the evaluation of the function of the central monoamine pathway is the comparison and the evaluation of changes in the level of central monoamine metabolism, the sensitivity to a drug that stimulates the central monoamine pathway, the presence of dysfunction of the mesolimbic dopamine pathway, the level of acclimation to new circumstances, or stress responsiveness.

3. The method for identifying a PTP-ζ inhibitor according to claim 2, wherein the mouse whose genome comprises a homozygous disruption of the PTP-ζ gene is backcrossed for 4 or more generations.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Sense Primer

<400> SEQUENCE: 1
ggtccactga agtccacagc                                                 20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:Antisense
      Primer

<400> SEQUENCE: 2
tctagtacaa tgtatgtgcc cg                                              22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:PTP-zeta
      Sense Primer

<400> SEQUENCE: 3
cgggagcttc ctggtcaacc ag                                              22

<210> SEQ ID NO 4
<211> LENGTH: 20
<212> TYPE: DNA
<213> ORGANISM: Artificial Sequence
```

```
-continued

<220> FEATURE:
<223> OTHER INFORMATION: Description of Artificial Sequence:PTP-zeta
      Antisense Primer

<400> SEQUENCE: 4
agcacgggta gggagtactc                                                      20
```